(12) United States Patent
Krishnan et al.

(10) Patent No.: US 10,175,232 B2
(45) Date of Patent: Jan. 8, 2019

(54) NUCLEOTIDE SEQUENCES, NUCLEIC ACID SENSORS AND METHODS THEREOF

(71) Applicant: NATIONAL CENTRE FOR BIOLOGICAL SCIENCES (NCBS-TIFR), Bangalore, Karnataka (IN)

(72) Inventors: Yamuna Krishnan, Bangalore (IN); Suruchi Sharma, Dehradun (IN)

(73) Assignee: National Centre For Biological Sciences (NCBS-TIFR), Bangalore (IN)

( * ) Notice: Subject to any disclaimer, the term of this patent is extended or adjusted under 35 U.S.C. 154(b) by 7 days.

(21) Appl. No.: 14/778,355

(22) PCT Filed: Apr. 15, 2014

(86) PCT No.: PCT/IB2014/060734
§ 371 (c)(1),
(2) Date: Sep. 18, 2015

(87) PCT Pub. No.: WO2015/033237
PCT Pub. Date: Mar. 12, 2015

(65) Prior Publication Data
US 2016/0370355 A1    Dec. 22, 2016

(30) Foreign Application Priority Data
Sep. 4, 2013   (IN) .......................... 3973/CHE/2013

(51) Int. Cl.
*C07H 21/00* (2006.01)
*G01N 33/53* (2006.01)
*C07H 21/04* (2006.01)
*G01N 33/569* (2006.01)

(52) U.S. Cl.
CPC ......... *G01N 33/5308* (2013.01); *C07H 21/00* (2013.01); *C07H 21/04* (2013.01); *G01N 33/5695* (2013.01)

(58) Field of Classification Search
None
See application file for complete search history.

(56) References Cited

U.S. PATENT DOCUMENTS

| 7,125,660 B2 * | 10/2006 | Stanton | ............... C12Q 1/6825 |
| | | | 435/4 |
| 2014/0220560 A1 * | 8/2014 | Jaffrey | ................ C12Q 1/6876 |
| | | | 435/6.1 |

FOREIGN PATENT DOCUMENTS

WO    2013016694 A2    1/2013

OTHER PUBLICATIONS

Koizumi (Biochemistry, 2000, vol. 39, pp. 8983-8992).*
Koizumi et al. Molecular recognition of cAMP by an RNA aptamer. Biochemistry, Aug. 1, 2000, vol. 39, No. 30, pp. 8983-8992. Abstract only.
International Search Report and Written Opinion for International Application No. PCT/IB14/60734, mailed.

* cited by examiner

*Primary Examiner* — Sarae L Bausch
(74) *Attorney, Agent, or Firm* — Kilpatrick Townsend & Stockton LLP

(57) ABSTRACT

The present disclosure relates to particular nucleotide sequences comprising of at least one stem and/or loop structure and which optionally bind fluorescent labels, for example DFHBI and a process for obtaining said sequences. The present disclosure also provides nucleic acid sensor for cAMP comprising reporter domain, communication module and target recognition domain. Further, the present disclosure provides for ratiometric sensors 10 for quantifying cAMP using the nucleic sensors of the instant invention. The instant disclosure further provides method for obtaining the sensors, method for detecting and measuring small molecules, such as cAMP using the sensors of the instant disclosure and kits thereof.

14 Claims, 12 Drawing Sheets

Specification includes a Sequence Listing.

A

B

NUCLEOTIDE SEQUENCES, NUCLEIC ACID SENSORS AND METHODS THEREOF

TECHNICAL FIELD

The instant disclosure relates to nucleotide sequences which comprise of atleast one stem and/or loop structure and which optionally bind fluorescent labels, for example, 3,5-difluoro-4-hydroxybenzylidene imidazolinone (DFHBI) and methods thereof. The instant disclosure also relates to the field of sensors. More particularly, the instant disclosure relates to a nucleic acid sensor for detecting and/or quantifying cyclic 3'-5' adenosine monophosphate (cAMP) and methods thereof. The instant disclosure further relates to a kit comprising the nucleotide sequence and nucleic acid sensor.

BACKGROUND OF THE DISCLOSURE

Genetically encoded sensors are very useful for imaging small molecules in living cells in order to detect them. The modular and programmable nature of nucleic acids, coupled with their capacity for molecular recognition, positions nucleic acids as a uniquely versatile scaffold for molecular sensing within the cellular milieu.

Cyclic adenosine monophosphate (3'-5'-cyclic adenosine monophosphate, cAMP) is a secondary messenger and is important in many biological processes. Thus, it becomes very important to detect and quantify cAMP in biological systems. Presently radio-immunoassays are being used for measuring cAMP in in vitro studies which are variable, costly and highly time consuming and the existing sensors for live cell imaging of cAMP are based on proteins which are natural intracellular targets of cAMP and hence these sensors may interfere with cellular physiology.

Modular RNA aptamer sensors generally known in the art have three domains: target recognition domain, communication module and reporter domain. Reporter domain comprises molecules that bind a fluorescent label, thus emitting a fluorescent signal. Target recognition domain binds the target to be detected and communication module transfers the information from target recognition domain to reporter domain such that whenever recognition domain binds to target, the reporter domain will give fluorescence signal.

Spinach is an RNA aptamer that binds the chromophore DFHBI. DFHBI, in general, is a chromophore with low fluorescence yields, i.e., it is very less fluorescent. However, when this chromophore is bound to Spinach, the fluorescence quantum yield increases by a factor of 80. This aptamer has a stem-loop called stem-loop-2, whose structure is important in order for binding to DFHBI but its sequence is not important. Stem loop-2 has been used as communication module for designing sensors for target analytes whose aptamers are known by attaching aptamer for the target analyte (which is target recognition domain) at stem loop-2.

However, RNA aptamers for various analytes have 5' ends that need to be free for their binding action e.g. cAMP aptamer. Spinach cannot be used as reporter domain for making sensors for such analytes as attaching aptamer to loop of stem-loop-2 will make analyte aptamer lose its 5' end. So, there is no Spinach based sensor for cAMP. Further, the available Spinach based aptameric sensors for cdiGMP, Adenosine, ADP SAM etc. are not ratiometric.

Therefore, in order to make Spinach aptamer amenable for such analytes, it is required to carry out a rearrangement in Spinach so as to create a free 5' end near stem-2. However, it is observed in the art that rearranging of nucleic acid molecules can affect their activity.

STATEMENT OF THE DISCLOSURE

Accordingly, the present disclosure relates to a nucleotide sequence comprising sequence set forth as SEQ ID No. 1, wherein N is base selected from group comprising A, G, U, C and modified base or any combinations thereof and number of bases vary from about 4 to about 9 bases, and the nucleotide sequence optionally binds to fluorescent dye; a method of obtaining nucleotide sequence as above, said method comprising acts of: (a) creating a nick in stem-loop 2 region of SEQ ID No. 24 to obtain stem-2 region with free 5' end and optionally varying nucleotide sequence of the stem-2 region to obtain the nucleotide sequence set forth as SEQ ID No. 1, and (b) optionally adding the fluorescent dye to the nucleotide sequence of step (a); a nucleic acid sensor for detecting target molecule, said sensor comprising (a) target recognition domain, and (b) reporter domain including communication module, comprises of nucleotide sequence as above and optionally hybridizes to fluorescently labelled DNA; a method of obtaining nucleic acid sensor as above, said method comprising acts of: (a) creating nick in stem-loop 2 region of SEQ ID No. 24 to obtain stem-2 region of reporter domain with free 5' end, and optionally varying nucleotide sequence of the stem-2 region, wherein the stem-2 region is communication module, (b) optionally extending, or splitting and extending the reporter domain, (c) obtaining target recognition domain, and (d) joining the target recognition domain to the free 5' end of the communication module to obtain the nucleic acid sensor; a method of identifying and optionally quantifying target molecule in a sample, said method comprising acts of: (a) contacting the sample with fluorescent dye, nucleic acid sensor as above, and optionally along with fluorescent label, (b) identifying the target molecule by determining the optical signal generated, and (c) optionally quantifying the target molecule by determining ratio of optical signal generated by fluorescent dye to fluorescent label; a kit for obtaining nucleotide sequence set forth as SEQ ID No. 1 or for obtaining nucleic acid sensor or for identifying and optionally quantifying target molecule in a sample, said kit comprising components selected from group of nucleotide sequence as above or reporter domain, sequence set forth as SEQ ID NO. 24, nucleic acid sensor as above, target recognition domain set forth as SEQ ID No. 23, fluorescently labelled DNA set forth as SEQ ID No. 19, free bases, fluorescent dye, fluorescent label, buffers, and instruction manual or any combinations thereof; and a method of assembling kit as above, said method comprising acts of combining components selected from group of nucleotide sequence as above or reporter domain, sequence set forth as SEQ ID NO. 24, nucleic acid sensor as above, target recognition domain set forth as SEQ ID No. 23, fluorescently labelled DNA set forth as SEQ ID No. 19, free bases, fluorescent dye, fluorescent label, buffers, and instruction manual or any combinations thereof.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

Figure 3:
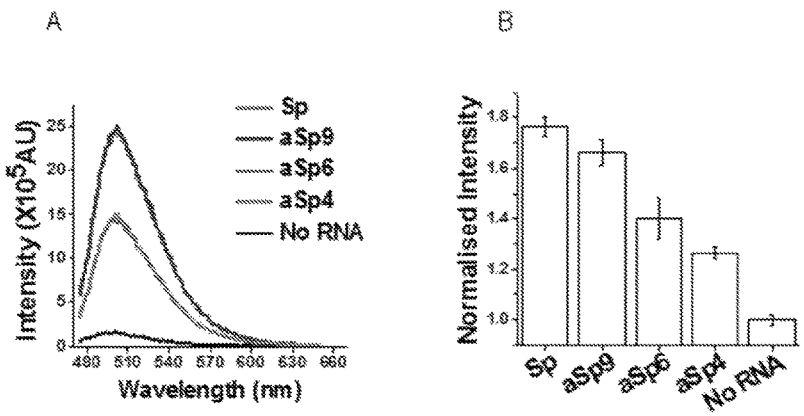

FIG. 3—'A' depicts a graph showing increase in fluorescence of DFHBI upon binding to the nucleotide sequences of the instant invention and 'B' is a bar graph showing the fold change in intensity of DFHBI upon binding to the nucleotide sequences of the instant disclosure.

FIG. 4 (a) depicts the process of obtaining RNA sequence of the nucleic acid sensor. FIGS. 4(b)-4(e) depicts the response of sensors (caSpn) of the instant invention to cAMP, wherein in (c), red line CaSp4, black line is CaSp7m and blue line is CaSpSb and in (e), black represents sensor CaSp7NE in the absence of cAMP and red represents CaSp7NE in presence of 2 mM cAMP.

Figure 5:
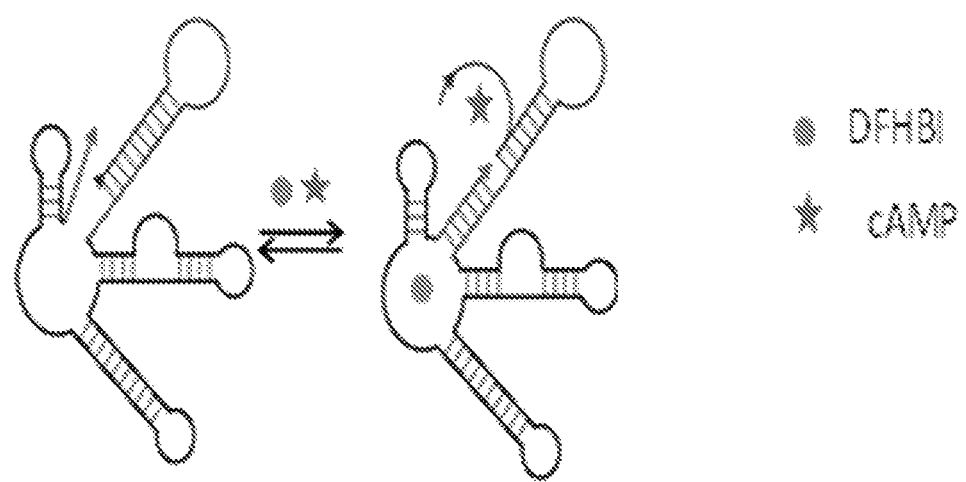

FIG. 5 depicts a schematic diagram showing the mechanism of sensing of the nucleic acid sensors of the instant disclosure.

FIG. 6—(a) depicts Strategy-1 for designing the ratiometric nucleic acid sensors of the instant disclosure (caSpn$^4$) and (b) depicts Strategy-2 for designing the ratiometric nucleic acid sensors (cAMPhor) of the instant disclosure.

FIG. 7—(a) depicts the detection of cAMP using the ratiometric sensors obtained by Strategy I of the instant disclosure, wherein Red line is CaSp7 m$^4$+2 mM cAMP, Black line is CaSp7 m$^4$+no cAMP, Green line is CaSp4$^4$+2 mM cAMP and Blue line is CaSp4$^4$+no cAMP; and (b) depicts graph showing the cAMP response of the sensors obtained by Strategy I (black line) and Strategy II (Red line).

Figure 8:
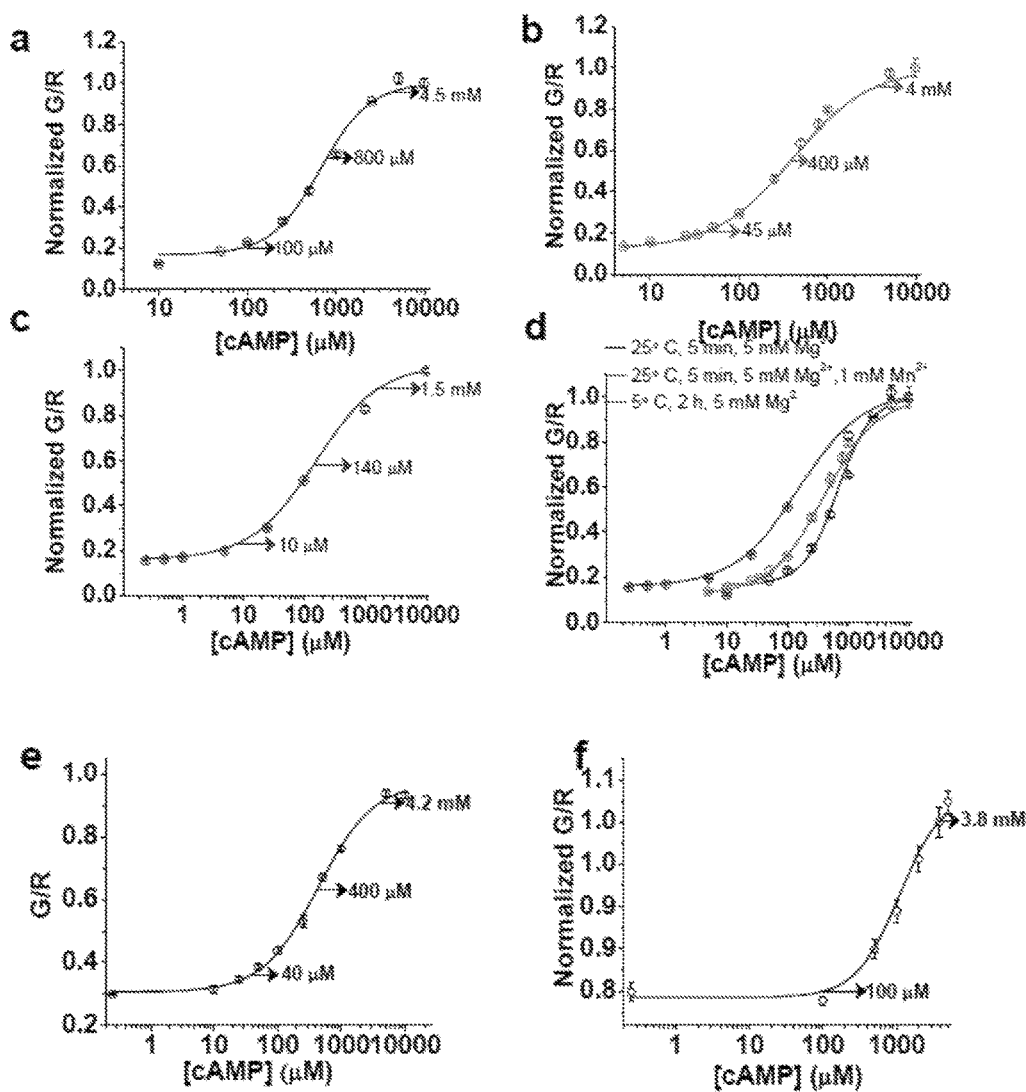

FIG. 8 depicts a graph showing the cAMP sensitivity of the ratiometric sensor of the instant disclosure under different conditions wherein 'a' represents cAMP sensitivity curve at 25° C. in about 5 minutes, 'b' represents cAMP sensitivity curve at 25° C. in presence of 1 mM Mn$^{2+}$ in about 5 minutes, 'c' represents cAMP sensitivity curve at 5° C. in about 2 hours, 'd' represents cAMP sensitivity curve at 25° C. (black), at 25° C. in presence of 1 mM Mn$^{2+}$ (red) and at 5° C. (blue) for comparison, 'e' represents cAMP sensitivity curve at 25° C. in about 2 hours, and 'f' represents cAMP sensitivity curve in presence of 5mMATPMg at 25° C. in about 2 hours.

Figure 9:
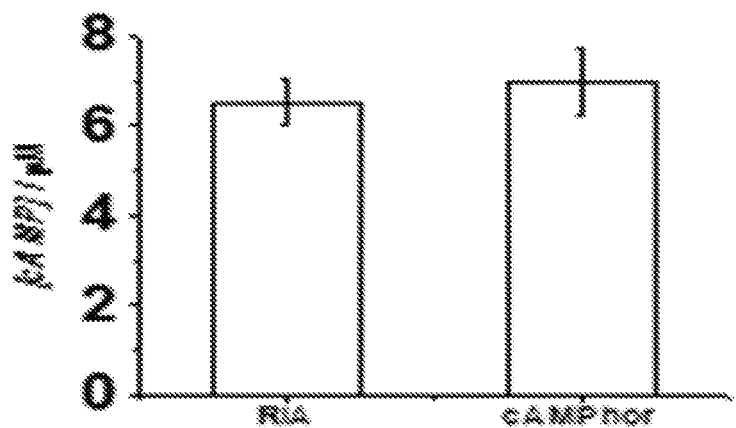

FIG. 9 depicts a bar graph showing the comparison of secreted cAMP measured using a radioimmunoassay and ratiometric sensor of the instant disclosure, wherein the values plotted are the mean±SEM of five different biological replicates.

Figure 10:
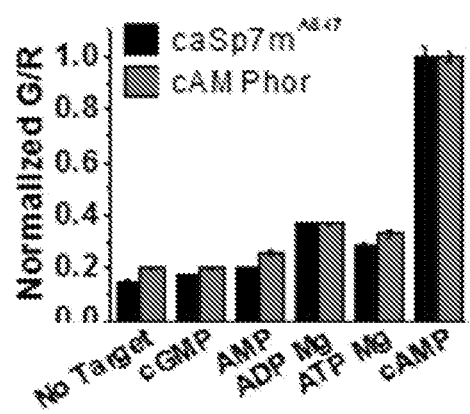

FIG. 10 depicts a bar graph showing the specificity of the ratiometric sensors of the instant disclosure wherein Normalized G/R values of cAMPhor is shown in red and of CaSp7 m$^4$ is shown in black.

Figure 11A:
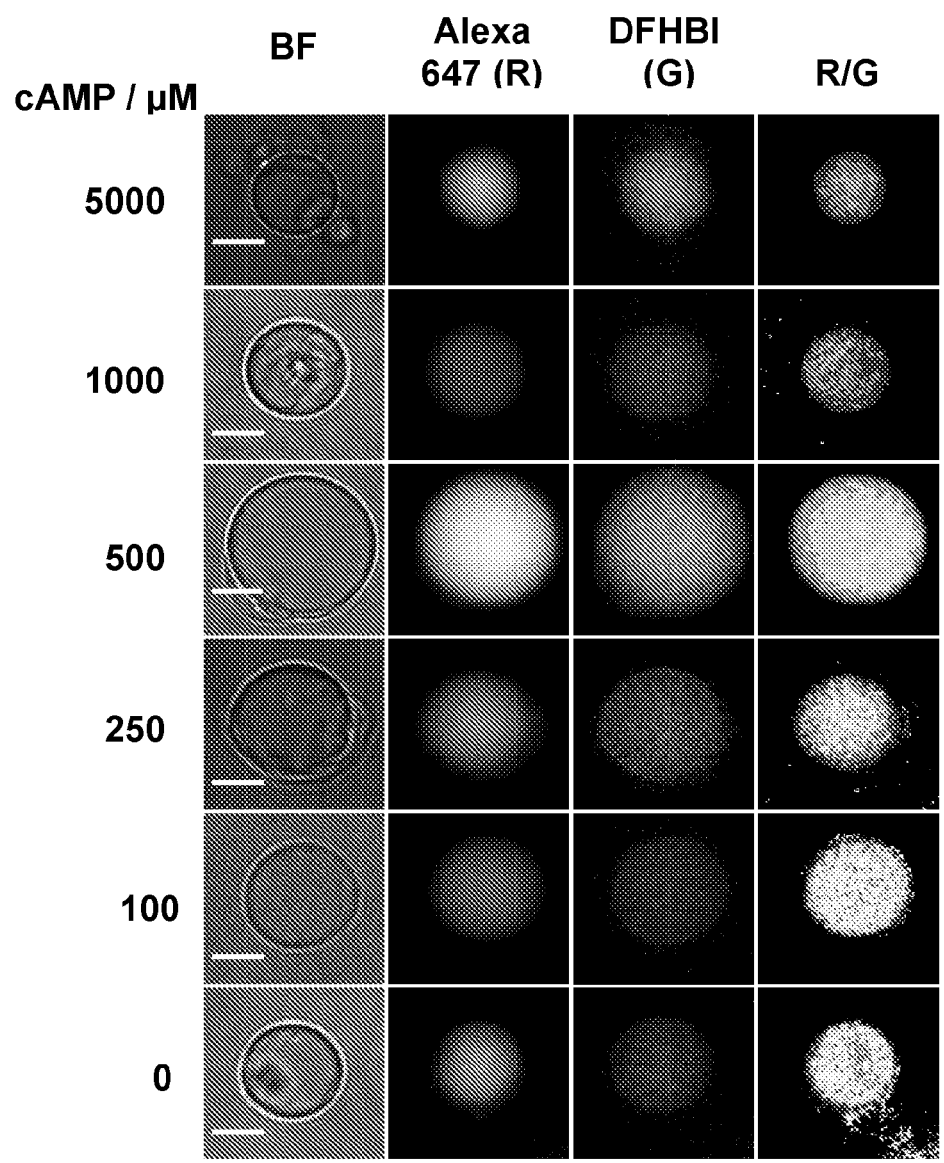
Figure 11B:
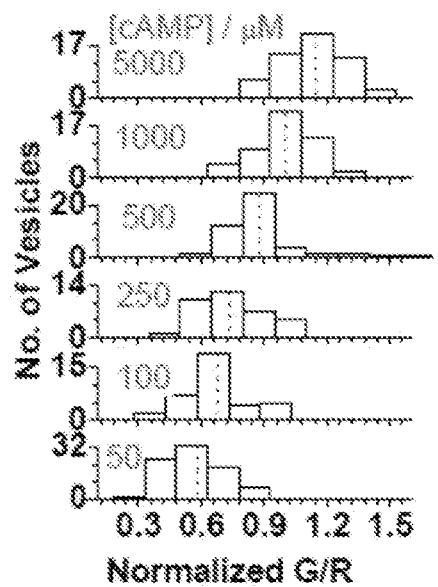

FIG. 11 depicts imaging of cAMP inside membrane bound compartments; (a) shows the bright field image (BF), images in Alexa 647 channel (R) and in DFHBI (G) channel of a given GUV containing 1 μM cAMPhor and indicated cAMP concentration as well as pseudocolored R/G images showing the ratio of R/G intensities of the above images. Scale bar: 5 μm. (b) depicts a histogram showing spread of normalized G/R values of a collection of GUVs at the indicated cAMP concentrations (n=at least 25). Red dotted line indicates the mean of each histogram; (c) shows the comparison of normalized G/R values obtained at various cAMP concentrations in solution and inside GUVs. The normalized G/R values reported for GUV is mean±s.e.m. of mean normalized G/R of at least three independent GUV preparations.

DETAILED DESCRIPTION OF THE DISCLOSURE

The present disclosure relates to a nucleotide sequence comprising sequence set forth as SEQ ID No. 1, wherein N is base selected from group comprising A, G, U, C and modified base or any combinations thereof and number of bases vary from about 4 to about 9 bases; and the nucleotide sequence optionally binds to fluorescent dye.

The present disclosure also relates to a method of obtaining nucleotide sequence as above, said method comprising acts of:
  (a) creating a nick in stem-loop 2 region of SEQ ID No. 24 to obtain stem-2 region with free 5' end and optionally varying nucleotide sequence of the stem-2 region to obtain the nucleotide sequence set forth as SEQ ID No. 1; and
  (b) optionally adding the fluorescent dye to the nucleotide sequence of step (a).

In an embodiment of the present disclosure, the modified base is selected from group comprising m$^5$G, m$^7$G, inosine and xanthosine or any combinations thereof.

In another embodiment of the present disclosure, said sequence comprises atleast one stem and/or loop structure and said nucleotide sequence generates an optical signal on optionally binding with the fluorescent dye, preferably 3, 5-difluoro-4-hydroxybenzylidene imidazolinone (DFHBI).

In yet another embodiment of the present disclosure, the nucleotide sequence has three stem loop structures and a stem structure with free 5' end.

In still another embodiment of the present disclosure, said nucleotide sequence is selected from group comprising SEQ ID No. 3, SEQ ID No. 4, SEQ ID No. 5, SEQ ID No. 6, SEQ ID No. 7 or SEQ ID No. 8.

The present disclosure further relates to a nucleic acid sensor for detecting target molecule, said sensor comprising:
  (a) target recognition domain; and
  (b) reporter domain including communication module; comprises of nucleotide sequence as above; and optionally hybridizes to fluorescently labelled DNA.

The present disclosure further relates to a method of obtaining nucleic acid sensor as above, said method comprising acts of:
  (a) creating nick in stem-loop 2 region of SEQ ID No. 24 to obtain stem-2 region of reporter domain with free 5' end; and optionally varying nucleotide sequence of the stem-2 region, wherein the stem-2 region is communication module;
  (b) optionally extending, or splitting and extending the reporter domain;
  (c) obtaining target recognition domain; and
  (d) joining the target recognition domain to the free 5' end of the communication module to obtain the nucleic acid sensor.

In an embodiment of the present disclosure, the target recognition domain has sequence set forth in SEQ ID No. 23 and binds to target molecule selected from group comprising small molecules, preferably cAMP.

In another embodiment of the present disclosure, the communication module is variable part of the reporter domain and is a linker between the recognition domain and the reporter domain; and sequence of the sensor is DNA, RNA or a combination thereof.

In yet another embodiment of the present disclosure, said sensor has nucleotide sequence set forth as SEQ ID No. 2; wherein N is base selected from group comprising A, G, U, C and modified base or any combinations thereof, and number of bases vary from about 4 to about 9 bases.

In yet another embodiment of the present disclosure, said sensor has nucleotide sequence selected from group comprising SEQ ID No. 9, SEQ ID No. 16, SEQ ID No. 22 and SEQ ID No. 15.

In yet another embodiment of the present disclosure, 3' end of the reporter domain of the sensor is extended and thereafter hybridized to the fluorescently labelled complementary DNA.

In yet another embodiment of the present disclosure, the reporter domain is split into two halves-Split A and Split B, 3' end of Split A and 5'end of Split B are extended and the extended Split B is hybridized to the fluorescently labelled complementary DNA.

In yet another embodiment of the present disclosure, said sensor has sequence set forth in SEQ ID No. 18; and the labelled complementary DNA has sequence set forth in SEQ ID No. 19.

In yet another embodiment of the present disclosure, said Split A has sequence set forth in SEQ ID No. 20 and said Split B has sequence set forth in SEQ ID No. 21; and the labelled complementary DNA has sequence set forth in SEQ ID NO. 19.

In yet another embodiment of the present disclosure, 3' end of the reporter domain is extended from about 15 to about 40 nucleotides, selected from group comprising A, C, U, T and G, or any combinations thereof to obtain extended reporter domain and hybridizing the extended reporter domain with the fluorescently labelled complementary DNA sequence.

In yet another embodiment of the present disclosure, the reporter domain is split into two halves—Split A and Split B; 3' end of the split A and 5' end of the split B are extended from about 15 to about 45 nucleotides selected from group comprising A, C, T, U, and G, or any combinations thereof and the extended Split B is hybridized with fluorescently labelled complementary DNA.

In still another embodiment of the present disclosure, the fluorescent label is selected from group comprising Alexa dye, bodipy dye, Cy3, Cy5, FITC and TAMRA, preferably Alexa dye.

The present disclosure further relates to a method of identifying and optionally quantifying target molecule in a sample, said method comprising acts of:
(a) contacting the sample with fluorescent dye, nucleic acid sensor as above, and optionally along with fluorescent label;
(b) identifying the target molecule by determining the optical signal generated; and
(c) optionally quantifying the target molecule by determining ratio of optical signal generated by fluorescent dye to fluorescent label.

In an embodiment of the present disclosure, the optical signal of step b) is generated by fluorescent dye bound to reporter domain of the sensor; and the target molecule is selected from group comprising small molecules, preferably cAMP.

In another embodiment of the present disclosure, the fluorescent dye is DFHBI; the fluorescent label in step (c) is attached to complementary DNA hybridized to reporter domain of the sensor; and the fluorescent label is selected from group comprising Alexa dye, bodipy dye, Cy3, Cy5, FITC and TAMRA, preferably Alexa dye.

In yet another embodiment of the present disclosure, the sample is biological sample selected or derived from group comprising cells, cell extracts, cell lysates, tissues, tissue extracts, bodily fluids, serum, blood and blood product, cAMP secreted in growth media.

The present disclosure further relates to a kit for obtaining nucleotide sequence set forth as SEQ ID No. 1 or for obtaining nucleic acid sensor or for identifying and optionally quantifying target molecule in a sample, said kit comprising components selected from group of nucleotide sequence as above or reporter domain, sequence set forth as SEQ ID NO. 24, nucleic acid sensor as above, target recognition domain set forth as SEQ ID No. 23, fluorescently labelled DNA set forth as SEQ ID No. 19, free bases, fluorescent dye, fluorescent label, buffers, and instruction manual or any combinations thereof.

The present disclosure further relates to a method of assembling kit as above, said method comprising acts of combining components selected from group of nucleotide sequence as above or reporter domain, sequence set forth as SEQ ID NO. 24, nucleic acid sensor as above, target recognition domain set forth as SEQ ID No. 23, fluorescently labelled DNA set forth as SEQ ID No. 19, free bases, fluorescent dye, fluorescent label, buffers, and instruction manual or any combinations thereof.

The present disclosure relates to a nucleotide sequence which comprises of atleast one stem and/or loop structure, optionally capable of binding to fluorescent dyes, such as DFHBI having low fluorescence quantum which upon binding, increases its fluorescence quantum yield. In an embodiment of the present disclosure, the nucleotide sequence comprises three stem-loop structures. The said nucleotide sequences may be used for designing sensors for small molecules whose aptamers are sensitive to manipulations at 5' ends, wherein the nucleotide sequences function as the reporter domain by binding fluorescent dye and emitting fluorescence.

In another embodiment, the present invention relates to nucleic acid sensors for detecting and quantifying small molecules, such as cAMP. The nucleic acid sensors comprise a target recognition domain which binds small molecules such as cAMP, a reporter domain for binding fluorescent label and a communication module which is part of the reporter domain whose sequence can be varied provided it forms a duplex. In an embodiment, the reporter domain of the nucleic acid sensor is the nucleotide sequence which comprises of atleast one stem and/or loop structure and binds to fluorescent dye, such as DFHBI. The target recognition domain is the RNA aptamer for cAMP, which is known in art (SEQ ID No.23) and the communication module is the stem region of the reporter domain with free 5' end; present within the reporter domain comprising the nucleotide sequence which is designed in such a way that it allows fluorescent dye such as DFHBI to bind the reporter domain only in the presence of cAMP. As a result, there is low fluorescence in absence and high fluorescence in the presence of cAMP.

Figure 2:
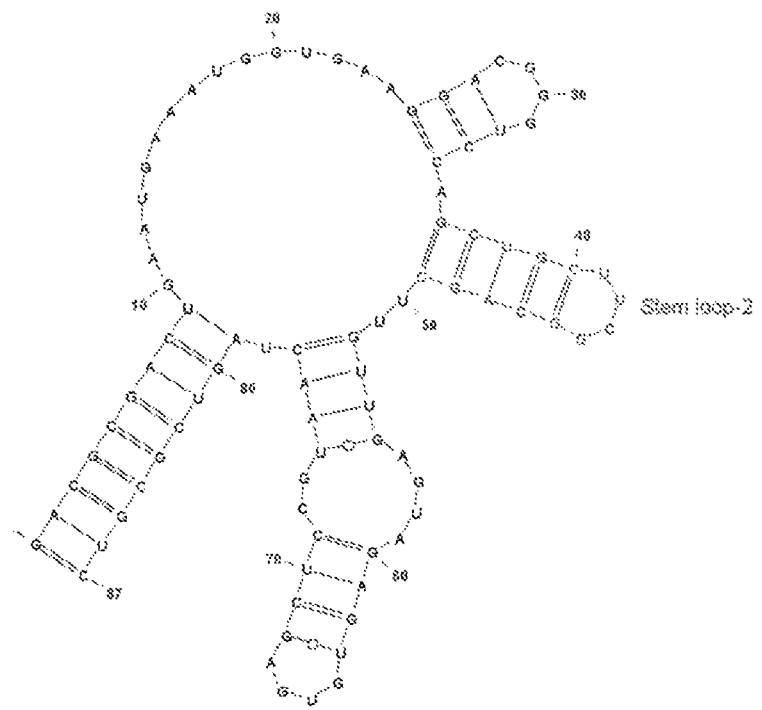
FIG. 2 depicts a structural representation of Spinach (2A) and the nucleotide sequence of the instant disclosure (2B).
Figure 2:
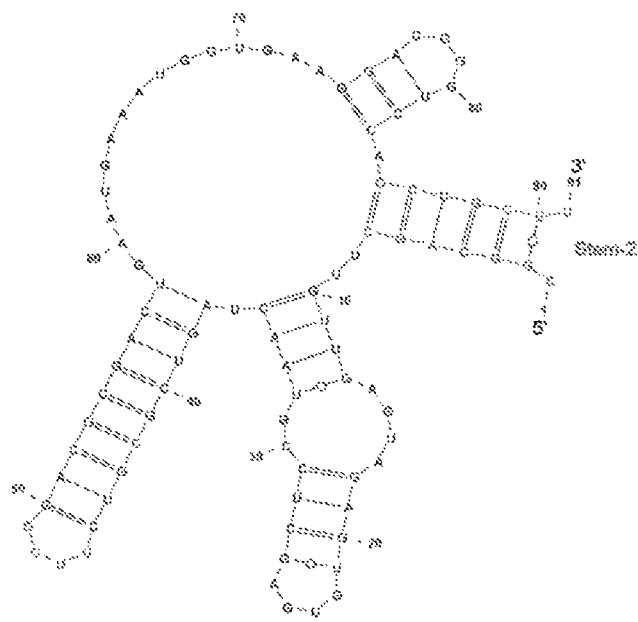

In an embodiment of the present disclosure, nucleotide sequence with atleast one stem and/or loop structure for binding to fluorescent dyes such as DFHBI are provided. This nucleotide sequence is modified form of the Spinach aptamer, particularly the nucleotide sequences are circular permuted versions of Spinach wherein a nick is created in loop-2 of Spinach (SEQ ID No. 24) to create a free 5'end and connecting the 5' and 3' end of the sequence by a 'UUCG' loop in order that it remains single stranded. FIG. 2(A) of the instant disclosure depicts the structure of Spinach while FIG. 2(B) depicts the structure of one of the nucleotide sequence of the instant invention which clearly shows the nick created in stem-loop 2 thereby creating a free 5' end in the sequence. The nucleotide sequence of the instant invention may be used to design sensors for molecules whose aptamers require free 5'end for binding to the molecules.

In an embodiment of the instant invention, on testing for the ability to enhance the fluorescence of DFHBI, it is found that molecules with shorter stem sequences are less effective in increasing the fluorescence of DFHBI, as compared to longer stem sequences thereby showing that shorter sequences which are less stable might result in loss of activity. Therefore, stability of Stem-2 is very crucial for the activity of the nucleotide sequence of the instant invention and designing of various such sequences is one of the aspects of the instant disclosure.

Figure 1:
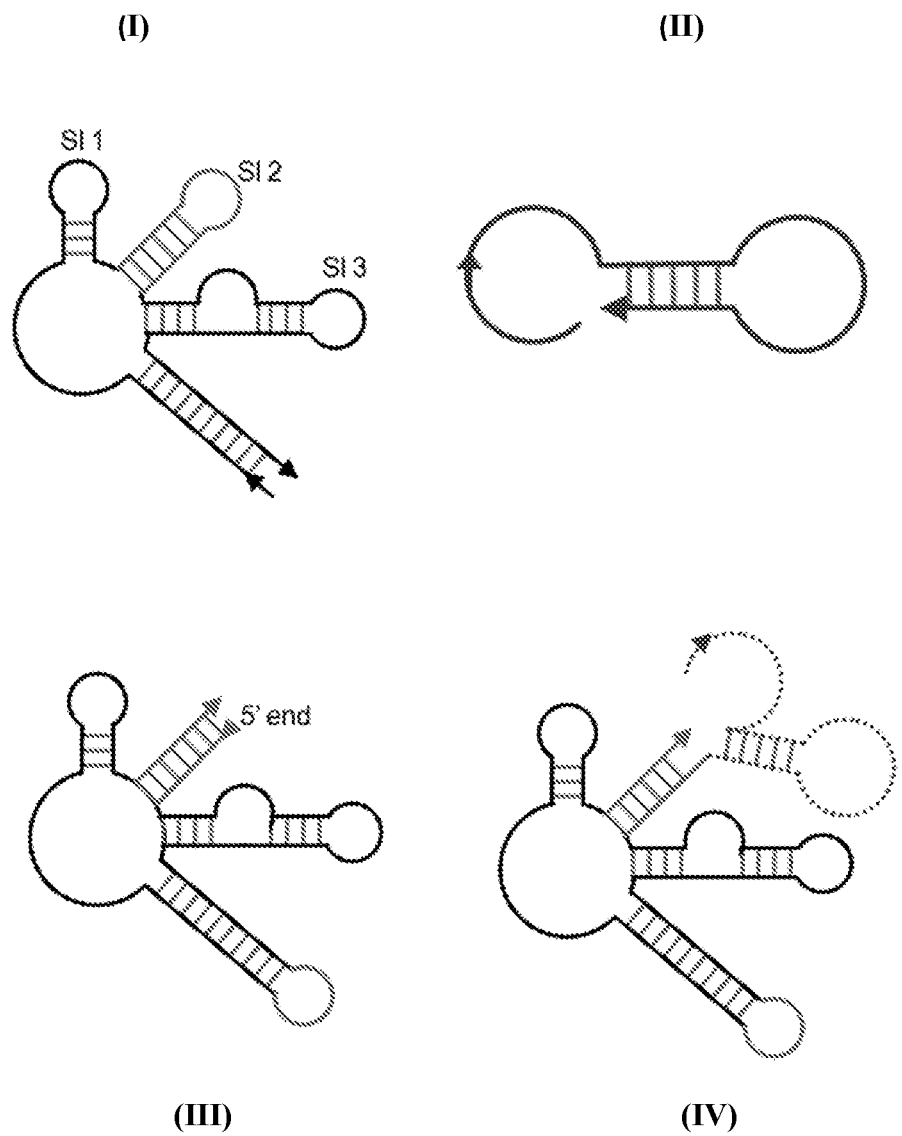
FIG. 1 depicts the basic design of the sensor of the instant disclosure, wherein (I) represents Spinach, (II) represents Class II cAMP RNA Aptamer, (III) represents nucleotide sequence of the instant disclosure and (IV) represents nucleic acid sensor of the instant disclosure.

The present disclosure also relates to nucleic acid sensors for detecting small molecules, such as cAMP. The nucleic acid sensors of the present disclosure are designed by linking/integrating/fusing/joining the 3' end of target recognition domain which is the RNA aptamer for cAMP (SEQ ID No. 23) to the 5' end of the reporter domain i.e., the nucleotide sequence of the instant invention. FIG. 1 depicts the designing of the nucleic acid sensor of the instant disclosure, wherein (I) depicts the basic structure of Spinach, (II) depicts Class II cAMP specific aptamer which functions as the target recognition domain, (III) depicts the nucleotide sequence of the instant invention which functions as the reporter domain and binds DFHBI and (IV) depicts the nucleic acid sensor of the instant disclosure wherein the cAMP aptamer is joined to the free 5' end of stem-2 region of the nucleotide sequence of the instant disclosure.

In another embodiment, many sequences were obtained by joining reporter domain and target recognition domain differing in communication module sequence. The communication module sequences vary in length from about 4 to about 9 base pairs, further mismatches are also created in them creating various communication module sequences. Of these, some of the sequences function as sensors by showing increase in fluorescence intensity of DFHBI only in the presence of cAMP and some do not show the functionality as sensors. Further, it is observed that those sequences that did not function as sensors for cAMP did not fold into proper secondary structures when entered into mfold as a functional sensor should as shown in FIG. 5 right conformation. Also these sequences have at least one secondary structure that did not change the structure of the reporter domain at any other place other than at communication module (e.g. FIG. 5 left conformation). Among those which are able to function as sensors for cAMP, the sensitivity, Signal/Noise and percentage change in signal (% SC) differ depending on the communication module sequences.

The mechanism of detection of cAMP by the nucleic acid sensor of the instant disclosure is depicted in FIG. 5 and is explained in detail below.

The nucleic acid sensor of the present disclosure is present in two conformations which exist in equilibrium with each other as shown in FIG. 5. As captured in the figure, the conformation on the left cannot bind to the fluorescence dye, such as DFHBI in the absence of cAMP, as half of the communication module, i.e., stem-2 of the reporter domain pairs with the target recognition module and a proper duplex is not formed. Thus, fluorescence exhibited by this molecule is less or negligible. However, in the presence of cAMP, the target recognition domain binds to cAMP, as a result of which a stable duplex of communication module is formed which in turn enables the binding of DFHBI to the reporter domain/nucleotide sequence (right conformation of FIG. 5). This molecule thus exhibits enhanced fluorescence.

In a further embodiment, the present disclosure provides ratiometric nucleic acid sensors that are capable of quantifying cAMP. Two different strategies are employed for designing such sensors as shown in FIG. 6.

Figure 6A:
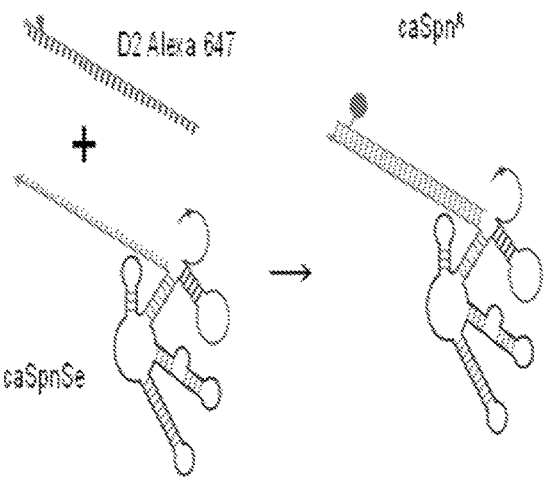

FIG. 6(a) depicts Strategy I, wherein the 3' end of the nucleic acid sensor is extended by about 15-40 nucleotide bases, preferably 38 nucleotide bases, and this extended end is hybridized with a complementary DNA oligonucleotide labelled with Alexa 647. Other dyes may also be used selected from group comprising FITC, TAMRA, Alexa 488, or any flurophore that can be conjugated to DNA.

Figure 6B:
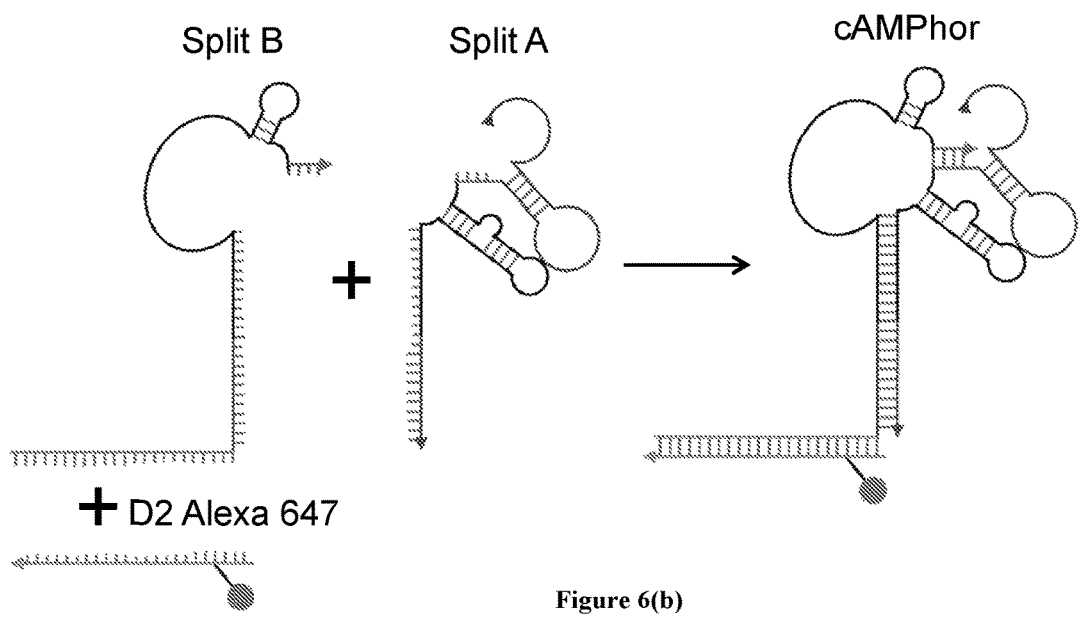

FIG. 6(b) depicts Strategy II, wherein the RNA of the nucleic acid sensor is split into two halves: Split A and Split B. About 15-45 nucleotide bases, preferably about 20 nucleotide bases are added to 3' end of Split A and complementary about 15-45 nucleotide bases, preferably about 20 nucleotide bases, are added to 5' end of Split B. The purpose of these extra nucleotide bases is to increase the strength of association of Split A and Split B. Further, 15-45 nucleotide bases, preferably about 38 more nucleotide bases complementary to Alexa 647 labelled DNA oligonucleotide are added to 5' end of Split B so as to facilitate the hybridization of Alexa 647 labelled DNA oligonucleotide to form a new trimeric assembly which can quantify cAMP in samples.

The principle of the functioning of the ratiometric sensors of the present disclosure is provided below:

In the normal sensors for detecting cAMP, the intensity at 501 nm obtained by binding cAMP depends on cAMP concentration as well as concentration of sensor RNA molecule. Therefore, this would not give an accurate estimation of the concentration of cAMP alone. Therefore, the ratiometric sensors of the present invention are designed with the objective of making it independent of RNA molecule concentration. For this purpose, Alexa 647 is attached to the sequence which is insensitive to cAMP concentration and whose intensity will thus be proportional to the sensor concentration alone. Thus, the ratio of fluorescence of DFHBI/fluorescence of Alexa 647 gives an accurate estimation of the concentration of cAMP. Said calculation is provided below:

Fluorescence of DFHBI $\alpha$ [cAMP] [Sensor]
Fluorescence of Alexa 647 $\alpha$ [Sensor]
DFHBI Fluorescence/Alexa 647 fluorescence $\alpha$ [cAMP]

It is essential to note here that although the examples provide specific sequences for extension of the nucleotide sequences of the ratiometric sensors for hybridizing with Alexa 647 labelled DNA, ratiometric sensors using other sequences of varying lengths for hybridizing with complementary DNA labelled with Alexa 647 also fall within the purview of the instant disclosure provided, the strength of association is strong enough under experimental conditions.

Table 1 below shows some the nucleotide sequences used in the present disclosure. The portions of the sequences in blue relate to the cAMP aptamer, portions of the sequences in red relate to the communication module and the portions of the sequences in green relate to the extended region of the reporter domain. However, it is important to note that other sequences formed by varying stem-2 and/or varying length of the extended region of the ratiometric sensors and/or any other variation in the sequence of the nucleotide sequence and the nucleic acid sensors will also fall within the scope of this invention as long as they retain the required activity.

TABLE 1

Sequences of the instant invention

| Name | SEQ ID No. | Sequence (5'-3')* |
|---|---|---|
| Nucleotide sequence of the instant disclosure | 1 | (N)nUUGUUGAGUAGAGUGUGAGCUCCGUAACUAGUCGCGUCUUCGGACGCGACUGAAU GAAAUGGUGAAGGACGGGUCCA(N)n |
| Nucleic acid sensor of the instant disclosure | 2 | GGAAGAGAUGGCGACUAAAACGACUUGUCGC(N)nUUGUUGAGUAGAGUGUGAGCUCCG UAACUAGUCGCGUCUUCGGACGCGACUGAAUGAAAUGGUGAAGGACGGGUCCA(N)n |
| achSpin (aSp6) | 3 | CGGCAGC UUGUUGAGUAGAGUGUGAGCUCCGUAACUAGUCGCGUC<u>UUC</u>GGACGCGACU GAAUGAAAUGGUGAAGGACGGGUCCAGCUGCUU |
| aSp9 | 4 | GGCAGGCACUUGUUGAGUAGAGUGUGAGCUCCGUAACUAGUCGCGUCUUCGGACGCGAC UGAAUGAAAUGGUGAAGGACGGGUCCAGUGUCUGCU |
| aSp4 | 5 | CAGCUUGUUGAGUAGAGUGUGAGCUCCGUAACUAGUCGCGUCUUCGGACGCGACUGAAU GAAAUGGUGAAGGACGGGUCCAGCUG |
| aSp7m | 6 | CAGGCACUUGUUGAGUAGAGUGUGAGCUCCGUAACUAGUCGCGUCUUCGGACGCGACUG AAUGAAAUGGUGAAGGACGGGUCCAGUGACUG |
| aSp5b | 7 | CAGCUUUGUUGAGUAGAGUGUGAGCUCCGUAACUAGUCGCGUCUUCGGACGCGACUGAA UGAAAUGGUGAAGGACGGGUCCAAGCUG |
| aSp6b | 8 | CAGCUCUUGUUGAGUAGAGUGUGAGCUCCGUAACUAGUCGCGUC<u>UUC</u>GGACGCGACUGA AUGAAAUGGUGAAGGACGGGUCCAGAGCUG |
| caSp4 | 9 | GGAAGAGAUGGCGACUAAAACGACUUGUCGCCAGCUUGUUGAGUAGAGUGUGAGCUCCG UAACUAGUCGCGUCUUCGGACGCGACUGAAUGAAAUGGUGAAGGACGGGUCCAGCUG |
| caSp5a | 10 | GGAAGAGAUGGCGACUAAAACGACUUGUCGCGCAGCUUGUUGAGUAGAGUGUGAGCUCC GUAACUAGUCGCGUCUUCGGACGCGACUGAAUGAAAUGGUGAAGGACGGGUCCAGCUGC |
| caSp6a | 11 | GGAAGAGAUGGCGACUAAAACGACUUGUCGCCGGCAGCUUGUUGAGUAGAGUGUGAGCU CCGUAACUAGUCGCGUCUUCGGACGCGACUGAAUGAAAUGGUGAAGGACGGGUCCA GCUGCUU |
| caSp7 | 12 | GGAAGAGAUGGCGACUAAAACGACUUGUCGCCAGGCACUUGUUGAGUAGAGUGUGAGCU CCGUAACUAGUCGCGUCUUCGGACGCGACUGAAUGAAAUGGUGAAGGACGGGUCCA GUGUCUG |
| caSp9m' | 13 | GGAAGAGAUGGCGACUAAAACGACUUGUCGCGGCAGGCACUUGUUGAGUAGAGUGUGAG CUCCGUAACUAGUCGCGUCUUCGGACGCGACUGAAUGAAAUGGUGAAGGACGGGUCCA GUGUGUGCU |
| caSp9m" | 14 | GGAAGAGAUGGCGACUAAAACGACUUGUCGCGGCAGGCACUUGUUGAGUAGAGUGUGAG CUCCGUAACUAGUCGCGUCUUCGGACGCGACUGAAUGAAAUGGUGAAGGACGGGUCCA GUGUCGGCU |
| caSp7m | 15 | GGAAGAGAUGGCGACUAAAACGACUUGUCGCCAGGCACUUGUUGAGUAGAGUGUGAGCU CCGUAACUAGUCGCGUCUUCGGACGCGACUGAAUGAAAUGGUGAAGGACGGGUCCA GUGACUG |
| caSp5b | 16 | GGAAGAGAUGGCGACUAAAACGACUUGUCGCCAGCUUUGUUGAGUAGAGUGUGAGCUCC GUAACUAGUCGCGUCUUCGGACGCGACUGAAUGAAAUGGUGAAGGACGGGUCCAAGCUG |
| caSp4A | 17 | GGAAGAGAUGGCGACUAAAACGACUUGUCGCCAGCUUGUUGAGUAGAGUGUGAGCUCCG UAACUAGUCGCGUCUUCGGACGCGACUGAAUGAAAUGGUGAAGGACGGGUCCA GCUGAUCAACACUGCACACCAGACAGCAAGAUCCUAUAUAUA |
| caSp7mA | 18 | GGAAGAGAUGGCGACUAAAACGACUUGUCGC CAGGCACUUGUUGAGUAGAGUGUGAGCU CCGUAACUAGUCGCGUCUUCGGACGCGACUGAAUGAAAUGGUGAAGGACGGGUCCA GUGACUGAUCAACACUGCACACCAGACAGCAAGAUCCUAUAUAUA |
| D2 Alexa 647 | 19 | TATATATAGGATCTTGCTGTCTGGTGTGCAGTGTTGAT |
| caSp4SplitA | 20 | GGAAGAGAUGGCGACUAAAACGACUUGUCGCCAGCUUGUUGAGUAGA GUGUGAGCUCCGUAACUAGUCGCGUCCGGCGUACCGUACCGUACCCUG |
| caSp4SplitB | 21 | AUCAACACUGCACACCAGACAGCAAGAUCCUAUAUAUACAGGGUACGG UACGGUACGCCGGACGCGACUGAAUGAAAUGGUGAAGGACGGGUCCA GCUG |

TABLE 1-continued

Sequences of the instant invention

| Name | SEQ ID No. | Sequence (5'-3')* |
|---|---|---|
| caSp6b | 22 | GGAAGAGAUGGCGACUAAAACGACUUGUCGCCAGCUCUUGUUGAGUA GAGUGUGAGCUCCGUAACUAGUCGCGUC UUCGGACGCGACUGAAUGAAAUGGUGAAGGACGGGUCCAGAGCUG |
| cAMP aptamer | 23 | GGAAGAGAUGGCGACUAAAACGACUUGUCGC |
| Spinach | 24 | GACGCGACUGAAUGAAAUGGUGAAGGACGGGUCCAGCUGCUUCGGCA GCUUGUUGAGUAGAGUGUGAGCUCCGUAACUAGUCGCGUC |
| caSp4DNA-1 | 25 | TAATACGACTCACTATAGGAAGAGATGGCGACTAAAACGACTTGTCGCCA GCTTGTTGAGTAGAGTGTGAGCTCCG |
| caSp4DNA-2 | 26 | CAGCTGGACCCGTCCTTCACCATTTCATTCAGTCGCGTCCGAAGACGCG ACTAGTTACGGAGCTCACACTCTACTC |
| caSp4SplitB DNA1 | 27 | TAATACGACTCACTATAGGGATCAACACTGCACACCAGACAGCAAGATCC TATATATACAGGGTACGGTACGG |
| caSp4SplitB DNA2 | 28 | CAGCTGGACCCGTCCTTCACCATTTCATTCAGTCGCGTCCGGCGTACCG TACCGTACCCTGTATATATAGGATC |
| FPcaSp4 | 29 | TAATACGACTCACTATAGGAAGAGA |
| RPcaSp4 | 30 | CAGCTGGACCCGTCCTTCACCATTTCATTC |
| FPIVTcaSpn | 31 | ATTCGCCCTTTAATACGACTCACTATAGGAAGAGA |
| RPcaSp5aPartA | 32 | TCTACTCAACAAGCTGCGCGACAAGTCG |
| FPcaSp5aPartB | 33 | CGACTTGTCGCGCAGCTTGTTGAGTAG |
| RPcaSp5a | 34 | GCAGCTGGACCCGTCCTTCACCATTTC |
| RPcaSp5bPartA | 35 | CTACTCAACAAAGCTGGCGACAAGTCG |
| FPcaSp5bPartB | 36 | CGACTTGTCGCCAGCTTTGTTGAGTAG |
| RPcaSp5b | 37 | CAGCTGGACCCGTCCTTCACCATTTC |
| RPcaSp6aPartA | 38 | TCTACTCAACAAGCTGCCGGCGACAAGTCG |
| FPcaSp6aPartB | 39 | CGACTTGTCGCCGGCAGCTTGTTGAGTAG |
| RPcaSp6a | 40 | AAGCAGCTGGACCCGTCCTTCACCATTTC |
| RPcaSp6bPart A | 41 | CTACTCAACAAGAGCTGGCGACAAGTCG |
| FPcaSp6bPartB | 42 | CGACTTGTCGCCAGCTCTTGTTGAGTAG |
| RPcaSp6b | 43 | CAGCTCTGGACCCGTCCTTCACCATTTC |
| RPcaSp7PartA | 44 | TCTACTCAACAAGTGCCTGGCGACAAGTCG |
| FPcaSp7PartB | 45 | ACGACTTGTCGCCAGGCACTTGTTGAGTAG |
| RPcaSp7 | 46 | CAGACACTGGACCCGTCCTTCACCATTTC |
| RPcaSp7m | 47 | CAGTCACTGGACCCGTCCTTCACCTTTC |
| RPcaSp9PartA | 48 | CTCTACTCAACAAGTGCCTGCCGCGACAAGTCG |
| FPcaSp9PartB | 49 | AACGACTTGTCGCGGCAGGCACTTGTTGAGTAGAG |
| RPcaSp9 | 50 | AGCAGACACTGGACCCGTCCTTCACC |
| RPcaSp9m | 51 | AGCACACACTGGACCCGTCCTTCACCTTTC |
| RPcaSp9m' | 52 | AGCACACACTGGACCCGTCCTTCACCTTTC |
| RPcaSp9m" | 53 | AGCCGACACTGGACCCGTCCTTCACCTTTC |
| FP caSp4SplitB | 54 | TAATACGACTCACTATAGGGATCAACACTG |
| RP caSp4SplitB | 55 | ATTCGCCCTTTAATACGACTCACTATAGGG |

TABLE 1-continued

Sequences of the instant invention

| Name | SEQ ID No. | Sequence (5'-3')* |
|---|---|---|
| RP caSp4SplitA | 56 | CAGGGTACGGTACGGTACGCCGGACGCGACTAGTTACGG |
| RP caSp4A | 57 | TATATATAGGATCTTGCTGTCTGGTGTGCAGTGTTGATCAGCTGGACCCG TCCTTCACC |
| RP caSp7mA | 58 | TATATATAGGATCTTGCTGTCTGGTGTGCAGTGTTGATAGTCACTGGACC CGTCCTTCACC |
| RPcaSp7nePartA | 59 | TCTACTCAACAAGTCCCTGGCGACAAGTCG |
| FPcaSp7nePartA | 60 | ACGACTTGTCGCCAGGGACTTGTTGAGTAG |
| RPcaSp7ne | 61 | AAGAGACTGGACCCGTCCTTCACCATTTC |
| caSp7ne | 62 | **GGAAGAGAUGGCGACUAAAACGACUUGUCGC*CAGGGAC*UUGUUGAGU AGAGUGUGAGCUCCGUAACUAGUCGCGUCUUCGGACGCGACUGAAUG AAAUGGUGAAGGACGGGUCCA*GUCUCUU*** |
| Duplex IVT DNA positive strand | 63 | ATTCGCCCTTTAATACGACTCACTATAGGAAGAGATGGCGACTAAAACGACT TGTCGCCAGCTTGTTGAGTAGAGTGTGAGCTCCGTAACTAGTCGCGTCTTC GGACGCGACTGAATGAAATGGTGAAGGACGGGTCCAGCTG |
| Duplex IVT DNA negative strand | 64 | TAAGCGGGAAATTATGCTGAGTGATATCCTTCTCTACCGCTGATTTTGCTGA ACAGCGGTCGAACAACTCATCTCACACTCGAGGCATTGATCAGCGCAGAAC CCTGCGCTGACTTACTTTACCACTTCCTGCCCAGGTCGAC |

*Duplex IVt DNA negatvie strand is in 3'-5'direction; remaining strands have been given in 5'-3'direction following the convention.

RP in the table denotes Reverse Primer and FP in table denotes Forward Primer. (N)n means a tract having any base selected from group comprising A, G, U, C and modified base or any combinations thereof and n indicates the number of bases that can vary from about 4-9 bases.

In D2 Alexa 647 (SEQ ID No. 19), the Alexa 647 is attached to the T shown in bold and italic and red. Additionally, '(N)n' may alternately be represented as 'N' wherein N is base selected from group comprising A, G, U, C and modified base or any combinations thereof and number of bases vary from about 4 to about 9 bases.

Further the Duplex IVT DNA positive strand set forth as SEQ ID No. 63 and the Duplex IVT DNA negative strand set forth as SEQ ID No. 64 together form the Duplex IVT DNA template having the following sequence:

```
5' ATTCGCCCTTTAATACGACTCACTATAGGAAGAGATGGCGACTAAG
   ||||||||||||||||||||||||||||||||||||||||||||||
   TAAGCGGGAAATTATGCTGAGTGATATCCTTCTCTACCGCTGATTT

AACGACTTGTCGCCAGCTTGTTGAGTAGAGTGTGAGCTCCGTAACT
   ||||||||||||||||||||||||||||||||||||||||||||||
   TGCTGAACAGCGGTCGAACAACTCATCTCACACTCGAGGCATTGAT

AGTCGCGTCTTCGGACGCGACTGAATGAAATGGTGAAGGACGGGTC
   ||||||||||||||||||||||||||||||||||||||||||||||
   CAGCGCAGAAGCCTGCGCTGACTTACTTTACCACTTCCTGCCCAGG

CAGCT
   |||||
   TCGAC 5'
```

In another embodiment of the instant disclosure, the nucleic acid sensors of the present disclosure can be delivered into cytoplasm by electroporation. They can also be used in genetically encodable formats which involves making cells express the sensors of the invention, followed by incubation of the cell in DFHBI to measure the cAMP concentration inside cytoplasm of the cell expressing the sensor of invention. Further, the sensors of the present disclosure can be targeted to various sub-cellular compartments for determining the concentration of cAMP in those compartments. This can be done by using a RNA-DNA hybrid in place of Split B RNA, wherein in the sensor designed by Strategy 2 described above, the portion complementary to D2 Alexa 647 is DNA instead of RNA. This would result in duplex DNA at the end of sensor which helps in targeting this sensor to various sub-cellular compartments.

The present disclosure is further elaborated with the help of following examples and associated figures. However, these examples should not be construed to limit the scope of the present disclosure.

EXAMPLES

Example 1: Effect of Stem-2 on the DFHBI Binding Activity of the Nucleotide Sequence Various nucleotide sequences for binding DFHBI are designed by varying the length of the stem-2 region of the nucleotide sequence of the instant invention in between 4-9 base pairs. The nucleotide sequences of interest (aSp9/aSp6/aSp4) and Sp at a concentration of about 2.5 µM in water is heated to 60° C. for 10 min followed by incubation in ice for 5 min. About 14.4 µL of this RNA is then added to about 345 µL solution of about 1× sensing buffer containing about 10 µM DFHBI. DFHBI emission spectra of this solution are acquired using $\lambda_{ex}$=469 nm. Fluorescence emission spectra shown in FIG. 3A shows that fluorescence emission of DFHBI increases upon binding to Sp (Spinach) 5 bases (5 bases are present in the stem of stemloop-2 of Sp), aSp9 (SEQ ID No. 4), aSp6 (SEQ ID No. 3), and aSp4 (SEQ ID No. 5) (named according to the number of base pairs in stem-2 region of the nucleotide sequence). In order to calculate the fold change in intensity of DFHBI upon binding to Sp, aSp9, aSp6 and aSp4, 100 nM of the RNA (Sp, aSp9/aSp6/aSp4) in water is heated to 60° C. for 10 min followed by incubation in ice for 5 min. About 36 μL of this RNA is then added to about 324 μL solution of about 1× sensing buffer containing about 10 μM DFHBI. DFHBI emission spectra of this solution are acquired using $\lambda_{ex}$=469 nm. DFHBI emission intensity at 501 nm of this solution is divided with the DFHBI emission intensity at 501 nm of the similar solution without nucleotide sequence to get the fold change as shown in FIG. 3B. From the figures it is clear that sequences with shorter stem sequences are less effective in increasing the fluorescence of DFHBI as compared to longer stem. Additionally sequences aSp7m (SEQ ID NO. 6), aSp5b (SEQ ID No. 7) and aSp6b (SEQ ID No. 8) also enable increase in fluorescence of DFHBI upon binding. This indicates that for the activity of the nucleotide sequences of the instant disclosure, the stability of Stem-2 is very crucial which is conferred upon by 4 to 9 number of base pairs in the stem, and not any random stem sequence and length will work.

Example 2: Preparation of RNA

1. Preparation of Template for IVT (In Vitro Transcription)

Figure 4A:
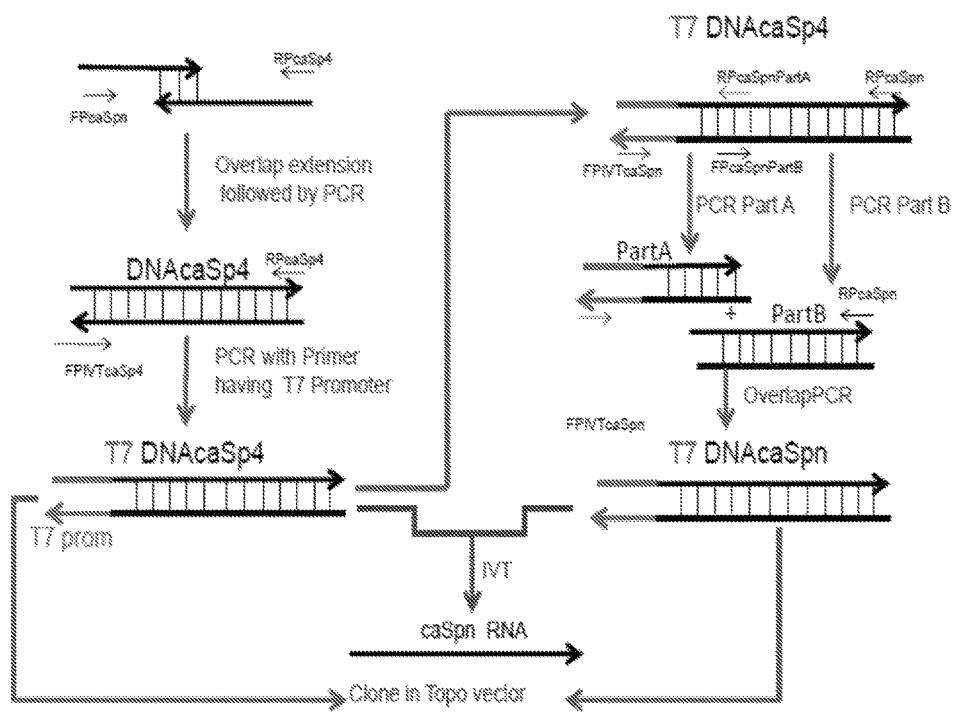

As depicted in FIG. 4(a), a duplex DNA sequence corresponding to the nucleic acid RNA sensors and T7 promoter at its 5' end is used as template for IVT to get the RNA. The IVT template for caSp4 is made by overlap extension PCR using two overlapping ss DNA oligonucleotides obtained from Sigma. These overlapping sequences are caSp4DNA-1 and caSp4DNA-2 shown in Table 1 (SEQ ID No. 25 and 26). This duplex DNA template is cloned in TopoTA vector using commercially available kit from Life Technologies, USA, i.e., TOPO® TA Cloning® Kit according to the manufacturer's instructions. The TopoTA vector carrying the IVT template for caSp4 as insert is transformed into E. coli DH5α cells. These cells are obtained from Life Technologies, USA (One Shot® MAX Efficiency™ DH5α-T1R). These transformed E. Coli are grown in media such as Luria Broth and plasmid is isolated from them. The sequence of the inserted template for IVT is confirmed by sequencing of the isolated plasmid. The inserted DNA is PCR amplified from the plasmid carrying the correct sequence using primers FPIVTcaSpn and RPcaSp4 shown in Table 1 (SEQ ID No. 31 and 30). This PCR product is ethanol precipitated and used as IVT template for getting RNA corresponding to caSp4. PCR reactions are carried out using 1 μM Forward Primer and Reverse Primer each using 0.3 U Pfu DNA polymerase, 0.2 mM dNTP and 5 ng of template DNA of interest, using 30 cycle PCR reaction involving the following steps:
1. Initial denaturation at 94° C. for 5 minutes
2. Denaturation at 94° C. for 1 minute
3. Annealing at 60° C. for 1 minute
4. Elongation at 72° C. for 1 minute
5. Steps (2), (3) and (4) are repeated 30 times
6. Final elongation is carried out at 72° C. for 5 minutes
7. Hold at 4° C.

IVT template for other constructs is made by modifying the IVT template for caSpn obtained as described ahead. For the constructs which need changes only at 3' end, PCR amplification is done using caSpn IVT template as PCR template using reverse primer RPcaSpn shown in Table 1 having desired change in the sequence. For those constructs that need changes in the middle, the entire construct is divided into two overlapping fragments namely, part A and part B, such that the changes needed in the sequence are at the ends of part A and part B. Part A is PCR amplified from IVT template of caSp4 using FPIVTcaSpn (SEQ ID No. 31) and RPcaSpnPartA and Part B is PCR amplified from IVT template caSpn using FPcaSpnPartB and RPcaSpn. Sequences of these primers are shown in Table 1. Overlap extension PCR is then done using about 5 ng of Part A and Part B each using FPIVTcaSpn and RPcaSpn. The PCR product obtained is cloned into TopoTA vector and transformed into E. coli DH5α cells as described earlier. E. Coli carrying plasmid is grown in media and plasmid is isolated from the bacteria and sequenced. From the plasmid carrying the correct sequence, template for IVT is made my PCR amplification using suitable forward primer (FPIVTcaSpn, SEQ ID No. 31), and reverse primer (RPcaSpn) (Table 1).

2. Preparation of RNA Using IVT (In Vitro Transcription)

About 100 ng of template for IVT for a given of caSpn is used for IVT using MEGAscript® T7 Transcription Kit from life technologies, USA according to manufacturer's instructions. Formation of intact RNA is confirmed by running on 10% denaturing PAGE in 0.5×TBE. If only single band of RNA is present, the IVT product is purified using NucAway™ Spin Column purchased from life technologies, USA according to manufacturer's instructions to remove unused NTPs and salt. NucAway purification is followed by ethanol precipitation. The precipitated RNA is resuspended in RNAase free water. RNA obtained now is quantified using OD $260_{nm}$. This RNA is used to study the cAMP sensing ability.

Example 3: Screening for RNA Constructs for cAMP Sensing Ability

Figure 4B:
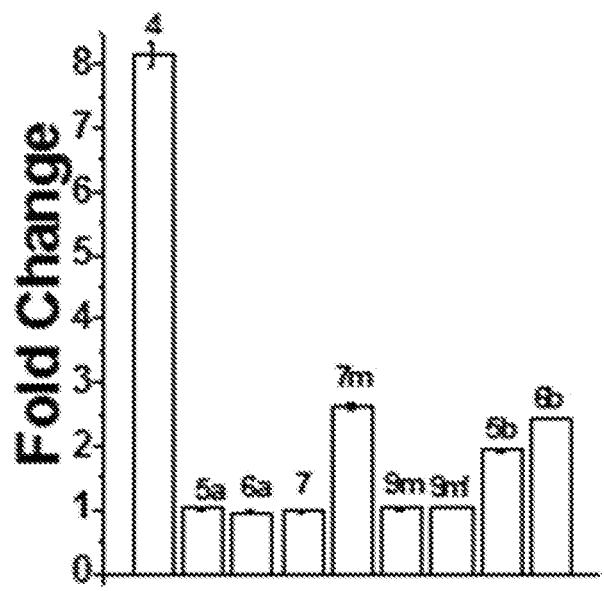

Various nucleic acid sensor sequences obtained by joining cAMP aptamer and modified DFHBI aptamer having varying length and sequence of stem-2 are synthesized and screened for their ability to enhance DFHBI fluorescence in the presence of cAMP. In this regard, various nucleic acid sensors are prepared by varying nucleotide sequences and length of stem-2 from 4 to 9 bp. Fluorescence emission spectra of about 360 μL solution of about 10 μM of DFHBI in about 1× sensing buffer with and without about 2 mM cAMP are acquired using $\lambda_{ex}$=469 nm and used as blank spectra. About 100 nM of the nucleic acid sensors (about 36 μL from about 1 μM stock in water) and about 10 μM of DFHBI (about 36 μL from about 100 μM stock) in about 1× sensing buffer (about 40 mM HEPES pH about 7.4, about 125 mM KCl and about 1 mM $MgCl_2$) are mixed in presence and absence of about 2 mM cAMP (about 36 μL from about 20 mM stock) in a total volume of about 360 μL. After 2 hours of incubation at about 25° C., fluorescence emission spectra are acquired using $\lambda_{ex}$ 469 nm. The corresponding blank spectra are subtracted from these spectra. After blank subtraction, emission intensity at 501 nm in presence of about 2 mM cAMP is divided by emission intensity at 501 nm in absence of cAMP and is reported as fold change. As seen in FIG. 4(b), few of the sequences did not respond to cAMP at all e.g. 5a (SEQ ID. No. 10), 6a (SEQ ID No. 11), 7 (SEQ ID No. 12), 9m (SEQ ID No.13) and 9m' (SEQ ID No. 14) (named so based on the length of the stem-2). Additionally, as can be seen from the FIG. 4(d), sensors with stem-2 of 6, 7 and 9 are highly fluorescent even in the absence of cAMP and thus not used as sensors. Further, as can be seen from FIG. 4(e), 7NE (SEQ ID No. 62) does not show any detectable change in signal in presence and absence of cAMP. Further, from FIGS. 4(b) and 4(d), it is clear that certain constructs, e.g., 4 (SEQ ID No. 9), 5b (SEQ ID No. 16), 7m (SEQ ID No. 15) and 6b (SEQ ID No. 22) respond to cAMP.

Example 4: cAMP Response Characteristics of Non-Ratiometric Sensors

The response characteristics of the RNA constructs that did respond to cAMP are studied in detail as described ahead. A 2.5 µM solution of nucleic acid sensor of interest (caSp4 (SEQ ID No. 9)/caSpSb (SEQ ID No. 16)/caSp7m (SEQ ID No. 15),) in about 1× annealing buffer (about 8 mM HEPES pH of about 7.4, about 20 mM NaCl and about 1 mM EDTA) with about 2.5 µM free Alexa 647 in a total volume of about 500 µL-1 mL is heated for about 10 minutes, followed by about 4 hour incubation at about 5° C. DFHBI and Alexa 647 fluorescence emission spectra of about 345 µL solution containing about 10 µM DFHBI, in about 1× sensing buffer, about 4 mM MgCl$_2$ and varying cAMP concentrations are acquired at 25° C. and taken as time t=0 spectra. Fluorescence emission spectra are taken using $\lambda_{ex}$=469 nm for DFHBI and for Alexa 647 using $\lambda_{ex}$=647 nm. Then, about 14.4 µL of about 2.5 µM stock solution of RNA sensor prepared as described above is added to this solution. DFHBI and Alexa 647 emission spectra are acquired again as described after t=5, 10, 15 and 30 minute of addition of sensor. Time t=0 spectra are used as blank and subtracted from all other time point spectra. After subtraction, emission intensity of DFHBI at 501 nm is divided by emission intensity of Alexa 647 at 670 nm to obtain normalized intensity. Normalized intensity (at t=5 minutes) is plotted as against respective cAMP concentrations for these RNA as shown in FIG. 4(c).

Figure 4C:
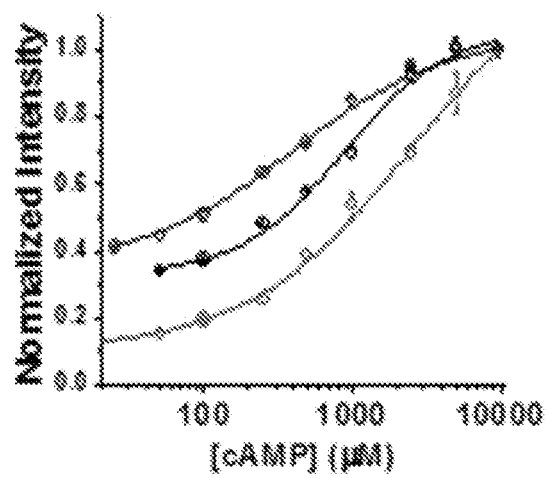
Figure 4D:
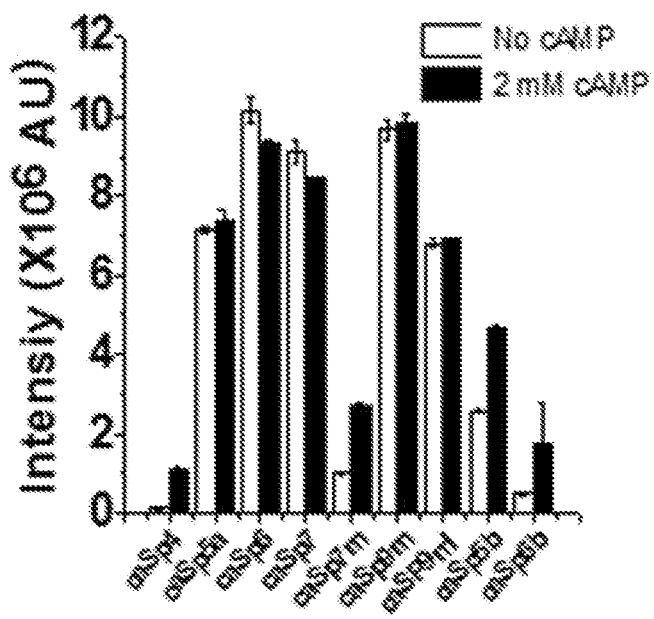
Figure 4E:
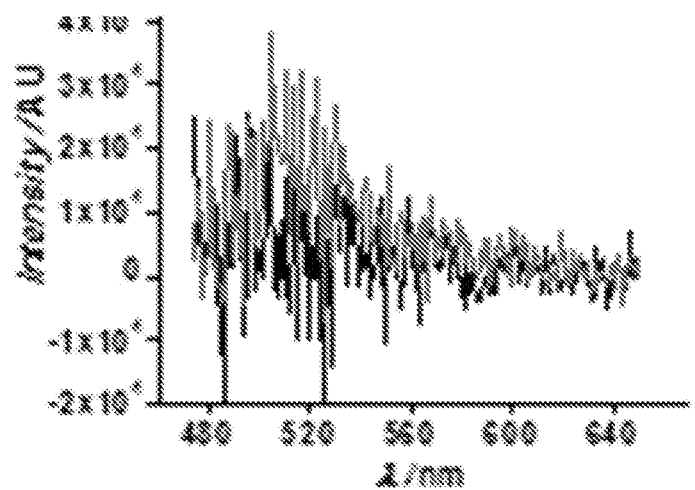

The response characteristics of these sensors vary in terms of percentage change in signal (% SC) cAMP sensitive regime as well as Signal/noise as shown in FIG. 4(c) and FIG. 4(d) and also shown in Table 2 below. This therefore confirms that the sensors of the present disclosure are able to detect cAMP and also shows the importance of the communication module in stabilizing the sensor and determining its activity.

TABLE 2 cAMP response characteristics the cAMP sensors indicating the cAMP concentration where 10-90% change in fluorescence emission of DFHBI takes place, EC$_{50}$ relates to the cAMP concentration where half maximal change in DFHBI fluorescence is observed and % change in signal (% SC) is percentage change in DFHBI fluorescence emission between two extreme cAMP concentrations.

| Name | 10%-90% change | EC$_{50}$ | % Signal Change (% SC) |
|---|---|---|---|
| caSp4 (5 min, 25° C.) | 100 µM-5 mM | 985 µM | 740% (0-9.7 mM) |
| caSp7m (5 min, 25° C.) | 80 µM-3.9 mM | 715 µM | 260% (0-9.7 mM) |
| caSp5b (5 min, 25° C.) | 25 µM-2.3 mM | 353 µM | 160% (0-9.7 mM) |

Example 5: Quantification of cAMP Using the Ratiometric Nucleic Acid Sensors

Figure 7A:
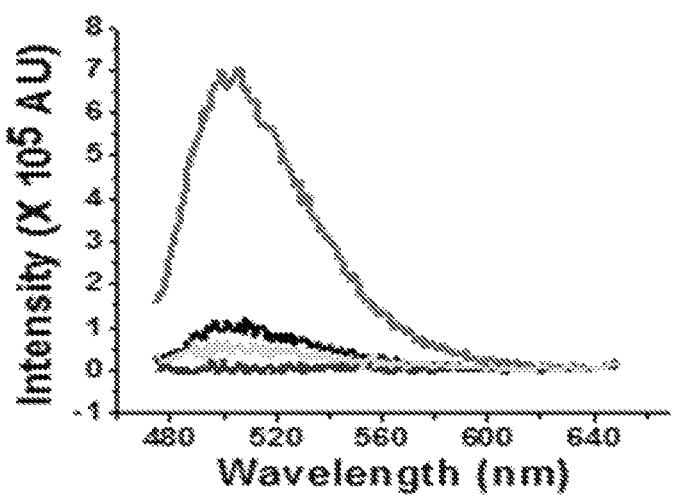

The various nucleotide sequences of the present disclosure are taken and further modified as per Strategy I to produce ratiometric sensors. Two of these sensors (SEQ ID No. 17 and SEQ ID No. 18) are then tested for their ability to detect cAMP as shown in FIG. 7(a) and tested for fluorescence in the presence and absence of cAMP. As seen in FIG. 7(a), one of the sensors (SEQ ID No. 18 or CaSp7 m$^A$) is able to sense cAMP, whereas the other sensor (CaSp4$^A$, SEQ ID No. 17) lost the DFHBI binding activity. This loss of activity of caSp4$^A$ is possibly because the extended 3' end creates a steric hindrance near sensing and communication module. To overcome the above drawback, ratiometric sensors are designed as per Strategy II.

Figure 7B:
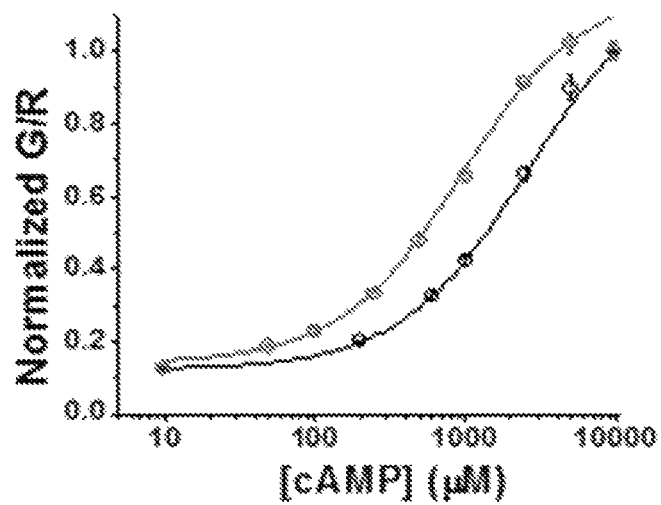

Ratiometric sensor samples are prepared by heating at about 60° C. about 2.5 µM solution of RNA (or two RNAs caSp4SplitA and caSp4SplitB in case of strategy II) in about 1× annealing buffer (about 8 mM HEPES pH of about 7.4, about 20 mM NaCl and about 1 mM EDTA) with about 2.5 µM D2Alexa 647 labelled DNA in a total volume of about 500 µL-1 mL for about 10 minutes, followed by about 4 hour incubation at about 5° C. DFHBI and Alexa 647 fluorescence emission spectra of about 345 µL solution containing about 10 µM DFHBI, in about 1× sensing buffer, about 4 mM MgCl$_2$ and varying cAMP concentrations are acquired at 25° C. and taken as time t=0 spectra. Fluorescence emission spectra are taken using $\lambda_{ex}$ 469 nm for DFHBI and for Alexa 647 using $\lambda_{ex}$ 647 nm. Then, about 14.4 µL of about 2.5 µM stock solution of sensor prepared as described above is added to this solution. DFHBI and Alexa 647 emission spectra are acquired as described earlier after t=5, 10, 15 and 30 minute of addition of sensor. Time t=0 spectra are used as blank and subtracted from all other time point spectra. After subtraction, emission intensity of DFHBI at 501 nm (G) is divided by emission intensity of Alexa 647 at 670 nm (R) to obtain G/R values. G/R values against respective cAMP concentrations for both the sensors (caSp7 m$^A$ (SEQ ID No. 18)) and (CaSp4split (SEQ ID No. 20-split A and SEQ ID NO. 21-splitB)) hybridized with Alexa 647 labelled DNA is plotted to get the cAMP response curve as shown in FIG. 7(b). Figure shows cAMP response curve for ratiometric sensor prepared by strategy I and caSp4split/cAMPhor (SEQ ID No. 20 and SEQ ID No. 21) hybridized with Alexa 647 labelled DNA (ratiometric sensor prepared by strategy II).

G/R values for caSp7 m$^A$ is at t=30 minutes and for caSp4split/cAMPhor is at t=5 minutes. From the figure, it is clear that the ratiometric sensors can quantify cAMP. The detailed cAMP response characteristics have been summarized in Table 3 below.

TABLE 3

Summary of the response characteristics of ratio metric sensors

| Name | 10%-90% change | EC$_{50}$ | % Signal Change (% SC) |
|---|---|---|---|
| cAMPhor (5 min, 25° C.) | 100 µM-4.5 mM | 800 µM | 690% (0 µM-9.7 mM) |
| cAMPhor (10 min, 25° C.) | 70 µM-3.2 mM | 524 µM | 470% (0 µM-9.7 mM) |
| cAMPhor (15 min, 25° C.) | 50 µM-2.7 mM | 456 µM | 390% (0 µM-9.7 mM) |
| cAMPhor (2 h, 25° C.) | 40 µM-4.2 mM | 403 µM | 213% (0.25 µM-10 mM) |
| cAMPhor (MnCl$_2$, 5 min, 25° C.) | 45 µM-4 mM | 400 µM | 669% (5 µM-9.7 mM) |

TABLE 3-continued

Summary of the response characteristics of ratio metric sensors

| Name | 10%-90% change | $EC_{50}$ | % Signal Change (% SC) |
|---|---|---|---|
| cAMPhor (5 mMATP, 25° C.) | 100 µM-3.8 mM | — | 25% (100 µM-3.8 mM) |
| cAMPhor (2 h, 5° C.) | 10 µM-1.5 mM | 140 µM | 510% (0.25 µM-10 mM) |
| cAMPhor (12 h, 5° C.) | 10 µM-1.5 mM | 260 µM | 110% (0.25 µM-10 mM) |
| caSp7m$^{4647}$ (30 min, 25° C.) | 250 µM-6.3 mM | 1.7 mM | 767% (0 µM-10 mM) |

Further, FIG. 8 shows the cAMP sensitivity of caSp4 split under different conditions. From the FIG. 8a, it can be seen that at room temperature, in about 1× sensing buffer, about 4 mM MgCl2 and about 10 µM DFHBI at about 25° C. in about 5 minutes, the sensors of the invention cAMPhor can measure cAMP from about 100 uM- to about 4.5 mM. From the FIG. 8b, it can be seen that in about 1× sensing buffer, about 4 mM MgCl$_2$, about 1 mM MnCl$_2$ and about 10 µM DFHBI at about 25° C. in about 5 minutes, the sensors of the invention cAMPhor can measure cAMP from about 45 µM to about 4 mM. From FIG. 8c, it can be seen that in about 1× sensing buffer, about 4 mM MgCl$_2$, and about 10 µM DFHBI at about 5° C. in about 2 hours, the sensors of the invention cAMPhor can measure cAMP from about 10 µM to about 1.5 mM. FIG. 8d shows the comparative graph of all three conditions. From FIG. 8e, it can be seen that in about 1× sensing buffer, about 4 mM MgCl$_2$, and about 10 µM DFHBI at about 25° C. in about 2 hours, cAMPhor can measure cAMP from about 40 µM to about 4.2 mM. Further, from FIG. 8f, it can be seen that in about 1× sensing buffer, about 4 mM MgCl$_2$, about 10 µM DFHBI and 5mMATPMg at about 25° C. in about 2 hours, cAMPhor can measure cAMP from about 100 µM to about 3.8 mM.

Example 6: Measurement of cAMP Secreted by Bacteria into Growth Media

*M. smegmatis* MC2155 obtained from USA is grown from glycerol stocks in 7H9 media supplemented with about 0.2% glycerol and about 0.05% Tween-80 at about 37° C. with shaking at about 180 rpm, till the culture reaches saturation. Cells are centrifuged at about 13000 rcf and washed with TBST (about 10 mM Tris-HCl (pH of about 7.5), about 0.89% NaCl, and about 0.05% Tween-80). Cells are re-suspended in original volume of fresh 7H9 media supplemented with about 0.2% glycerol and about 0.05% Tween-80. To this suspension, Sodium Dodecyl Sulphate (SDS) is added to achieve a final concentration of about 0.05%. This suspension is allowed to grow for about 1.5 hours at about 37° C. After about 1.5 hours, cells are centrifuged at about 13000 rcf and the cell free supernatant is recovered. An aliquot of the supernatant is acidified with HCl at a final concentration of about 0.1N, boiled for about 10 minutes and used for radioimmunoassay. The remaining supernatant is boiled and used for measurements with caSp4split. Measurements using about 100 nM caSp4split at about 5° C. in about 1× sensing buffer+about 10 µM DFHBI+about 4 mM MgCl2 and G/R values are taken at t=2 hours as described earlier. Samples are spun at about 10000 rcf for about 4 minutes immediately before acquiring the fluorescence spectra. As can be observed from FIG. 9, the cAMP concentration measured using caSp4Split matched well with values obtained using standard radioimmunoassay technique thus validating that caSP4Spilt can measure unknown cAMP concentrations in complex biological mixtures provided they lie in sensitive regime.

Example 7: Specificity of Ratiometric Sensors

Ratiometric sensor samples are prepared by heating about 2.5 µM solution of RNA (or two RNAs caSp4SplitA and caSp4SplitB in case of strategy II) in about 1× annealing buffer (about 8 mM HEPES pH of about 7.4, about 20 mM NaCl and about 1 mM EDTA) with about 2.5 µM D2Alexa 647 labelled DNA in a total volume of about 500 µL-1 mL for about 10 minutes, followed by about 4 hour incubation at about 5° C. DFHBI and Alexa 647 fluorescence emission spectra of about 345 µL solution containing about 10 DFHBI, in about 1× sensing buffer, about 4 mM MgCl$_2$ and structural variant of cAMP (ATP/ADP/AMP/cGMP) at about 25° C. are taken as time t=0 spectra. Fluorescence emission spectra are taken using $\lambda_{ex}$=469 nm for DFHBI and for Alexa 647 using $\lambda_{ex}$ 647. Then, about 14.4 µL of about 2.5 µM stock solution of sensor prepared as described above is added to this solution. DFHBI and Alexa 647 emission spectra are acquired as described earlier after t=5, and 30 minute of addition of sensor. Time t=0 spectra are used as blank and subtracted from all other time point spectra. After subtraction, emission intensity of DFHBI at 501 nm (G) is divided by emission intensity of Alexa 647 at 670 nm (R) to obtain G/R values. G/R values obtained in the presence of structural variants of cAMP are divided by the corresponding G/R values for equi-molar cAMP concentration to get normalized G/R value against respective sensors (FIG. 10). FIG. 10 shows normalized G/R values for structural variants of cAMP of the sensor prepared by strategy I (caSp7 m$^4$) and caSp4split/cAMPhor (SEQ ID No. 20 and SEQ ID No. 21) hybridized with Alexa 647 labelled DNA (ratiometric sensor prepared by strategy II).

Normalized G/R values for caSp7 m$^4$ is at t=30 minutes and for caSp4split/cAMPhor is at t=5 minutes. From the figure, it is clear that the ratiometric sensors are specific for cAMP.

Example 8: cAMP Imaging Inside Membrane Bound Compartments

Figure 11C:
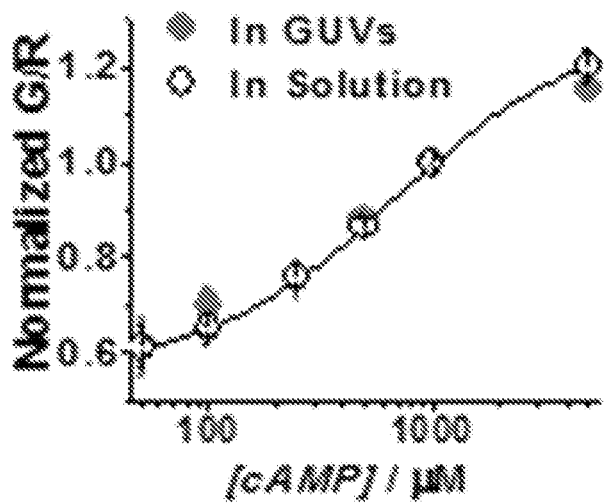

To determine the ability of cAMPhor for imaging cAMP in model membrane-bound vesicles, giant Unilamellar Vesicles (GUVs) are prepared from DMPC lipids (1,2-dimyristoyl-sn-glycero-3-phosphocholine) encapsulating about 1 µM cAMPhor, about 50 µM DFHBI and varying concentrations of cAMP in about 1× sensing buffer pH of about 6.8, about 4 mM MgCl$_2$ and about 500 mM sucrose. The response curve for cAMPhor in bulk solution under identical conditions is constructed. cAMPhor retained its 100 µM-4.5 mM sensitive regime with an overall % SC of ~100% as shown in FIG. 11(c) (open circles). GUVs containing cAMPhor, DFHBI and cAMP at the indicated concentrations are imaged under a fluorescence microscope in bright field (BF), DFHBI (G) and Alexa 647 (R) channels. The images acquired in R channel are divided by the corresponding images in G channel and pseudocolored into 16 colours to get R/G images (FIG. 11(a)). These clearly revealed decreasing R/G values as the cAMP inside the GUVs increases. The frequency histogram of normalized G/R ratios of individual GUVs (n~25) at the indicated cAMP concentrations showed with high clarity, the expected shifts towards higher G/R values with increasing cAMP concentrations (FIG. 11(b)). Moreover, the mean G/R from three different experiments correlated well with the expected G/R values in bulk solution for every concentration of elevated cAMP tested as shown in FIG. 11(c). This confirms that cAMPhor can image cAMP quantitatively inside membrane bound compartments.

Example 9: Comparison of the Sensors of the Instant Invention with the Existing Sensors for cAMP The % signal change of the sensor of the instant invention is very high and it measures above 100 uM levels of cAMP as can be observed from FIG. 7(b) explained in Example 5. It is observed from the prior art, that the sensors presently known in art cannot measure this high cAMP concentrations. The cAMP sensor of present invention helps in measuring elevated cAMP levels that are present at various pathological conditions and infections. None of the existing sensors of the prior art have comparable % SC to the present sensor. Also the % signal change (% SC) shown by sensors is much higher than existing cAMP sensors for live cell imaging of cAMP as shown in table 4 below.

TABLE 4

Summarising the cAMP sensors known in art and one the cAMP sensors of the present invention in order to facilitate the comparison.

| Motif | Conditions | Sensitivity regime | % SC |
|---|---|---|---|
| PKA (Protein) | 5 mM Mg$^{2+}$, 3 mM ATP, 22° C. 125 mM NaCl, 5 mM KCl, 1 mM Na3PO4, 1 mM MgSO4, 5.5 mM glucose and 20 mM HEPES pH 7.4, RT | 0.02-5 µM 10-100 µM | ~20% ~20% |
| Epac (Protein) | 140 KCl, 5 NaCl, 1 MgCl2 and 10 Mm HEPES pH 7.2 5 mMTris-HCl pH 7.3, 2 mM EDTA | 5-100 µM 0.1-10 µM | ~30% ~30% |
| CNGC (Protein) | In isolated cells | 0.5-100 µM | ~20% |
| Sensor of the present disclosure | at 25° C. for 2 hours in presence of 5 mM ATPMg at 25° C. for 2 hours | 0.04-4.2 mM 0.1-3.8 mM | ~200% ~25% |

Thus, it is clear from the above examples and figures that the sensors of the instant disclosure are highly useful for detecting and quantifying cAMP. Further, the sensors of the instant disclosure may be used in various applications such as, but not limiting to:
  Measuring cAMP in in vitro assays, wherein one is interested in measuring the amount of either secreted or intracellular accumulated cAMP by a population of cells;
  Visualizing and measuring levels of cAMP in both prokaryotic and eukaryotic cells;
  Monitoring the elevation in cAMP levels (cAMP burst) that occurs during various pathogen infections;
  For studying the role of cAMP in compartmentalization of eukaryotic cells, where cAMP regulates diverse cellular processes in such cells;
  For studying the activity of adenylyl cyclase and hence for screening to identify inhibitors and activators of this enzyme. This has direct application in screening for drug molecules.
  Further, the sensors of the instant disclosure are targeted to various compartments inside cells including by interfacing them with DNA, proteins and other small molecules.

While a number of embodiments and examples of this invention are described herein, it is apparent that these embodiments and examples may be altered to provide additional embodiments and examples which use the processes of this invention.

We claim:
1. A nucleotide sequence comprising SEQ ID NO: 1, wherein the nucleotide sequence optionally binds to fluorescent dye.
2. A method of obtaining the nucleotide sequence as claimed in claim 1, said method comprising the steps of:
   a. creating a nick in SEQ ID NO: 24 and varying the nucleotide sequence to obtain the nucleotide sequence comprising SEQ ID NO: 1; and
   b. optionally adding a fluorescent dye to the nucleotide sequence of step (a).
3. The method of claim 2, wherein the modified bases are selected from the group consisting of $m^5G$, $m^7G$, $inosine_a$ and xanthosine.
4. The method of claim 2, wherein the sequence comprises at least one stem and loop structure, generates an optical signal upon binding with the fluorescent dye; and wherein the nucleotide sequence is selected from SEQ ID NO: 3, SEQ ID NO: 4, SEQ ID NO: 5, SEQ ID NO: 6, SEQ ID NO: 7 or SEQ ID NO: 8.
5. A nucleic acid sensor for detecting a target molecule, the sensor comprising a target recognition domain and a reporter domain, wherein the reporter domain comprises the nucleotide sequence of SEQ ID NO: 1.
6. A method of obtaining a nucleic acid sensor as claimed in claim 5, said method comprising the steps of:
   a. creating a nick in SEQ ID NO: 24 and varying the nucleotide sequence to obtain a reporter domain comprising the nucleic acid sequence of SEQ ID NO: 1;
   b. obtaining a target recognition domain; and
   c. joining the target recognition domain to the reporter domain to obtain the nucleic acid sensor of claim 5.
7. The method of obtaining the nucleic acid sensor as claimed in claim 6, wherein the target recognition domain has sequence set forth in SEQ ID NO: 23 and binds to small molecules.
8. The method of obtaining nucleic acid sensor as claimed in claim 6, wherein the sensor comprises the nucleotide sequence selected from the group consisting of SEQ ID NO: 9, SEQ ID NO: 15, SEQ ID NO: 16, and SEQ ID NO: 22.
9. The method of obtaining the nucleic acid sensor as claimed in claim 6, wherein 3' end of the reporter domain is extended from about 15 to about 40 nucleotides and hybridizing the extended reporter domain with a fluorescently labelled complementary DNA sequence; and wherein the fluorescent label is selected from the group consisting of Alexa dye, bodipy dye, Cy3, Cy5, FITC and TAMRA.
10. A kit for obtaining the nucleotide sequence comprising SEQ ID NO: 1, a nucleic acid sensor, or for identifying and optionally quantifying target molecule in a sample; the kit comprising a nucleic acid sequence comprising the sequence of SEQ ID NO: 1 and any combination of the following components: a nucleotide sequence comprising the sequence of SEQ ID NO: 19, SEQ ID NO: 23, or SEQ ID NO: 24: nucleotide bases; fluorescent dye; fluorescent label; buffers; and instruction manual.
11. The nucleotide sequence of claim 1, wherein the modified bases are selected from the group consisting of $m^5G$, $m^7G$, $inosine_a$ and xanthosine.
12. The nucleotide sequence of claim 1, wherein the nucleotide sequence is selected from the group consisting of SEQ ID NO: 3, SEQ ID NO: 4, SEQ ID NO: 5, SEQ ID NO: 6, SEQ ID NO: 7, and SEQ ID NO: 8.
13. The nucleic acid sensor of claim 5, wherein the target recognition domain comprises the nucleotide sequence of SEQ ID NO: 23 and binds to a target molecule.
14. The nucleic acid sensor of claim 5, wherein the sensor comprises the nucleotide sequence selected from the group consisting of SEQ ID NO: 9, SEQ ID NO: 15, SEQ ID NO: 16, and SEQ ID NO: 22.

* * * * *

SEQUENCE LISTING

<160> NUMBER OF SEQ ID NOS: 64

<210> SEQ ID NO 1
<211> LENGTH: 79
<212> TYPE: RNA
<213> ORGANISM: Artificial Sequence
<220> FEATURE:
<223> OTHER INFORMATION: synthetic nucleotide sequence
<220> FEATURE:
<221> NAME/KEY: misc_feature
<222> LOCATION: (1)..(79)
<223> OTHER INFORMATION: n is base selected from group comprising A, G,
      U, C and modified base  or any combinations thereof and number of
      bases vary from about 4 to about 9 bases

<400> SEQUENCE: 1
nuuguugagu agagugugag cuccguaacu agucgcgucu ucggacgcga cugaaugaaa      60
uggugaagga cggguccan                                                  79

```
<210> SEQ ID NO 2
<211> LENGTH: 110
<212> TYPE: RNA
<213> ORGANISM: Artificial Sequence
<220> FEATURE:
<223> OTHER INFORMATION: synthetic nucleic acid sensor
<220> FEATURE:
<221> NAME/KEY: misc_feature
<222> LOCATION: (1)..(110)
<223> OTHER INFORMATION: n is base selected from group comprising A, G,
      U, C and modified base or any combinations thereof and number of
      bases vary from about 4 to about 9 bases

<400> SEQUENCE: 2
ggaagagaug gcgacuaaaa cgacuugucg cnuuguugag uagaguguga gcuccguaac        60
uagucgcguc uucggacgcg acugaaugaa auggugaagg acgggguccan                110

<210> SEQ ID NO 3
<211> LENGTH: 91
<212> TYPE: RNA
<213> ORGANISM: Artificial Sequence
<220> FEATURE:
<223> OTHER INFORMATION: synthetic nucleotide aSp6
<220> FEATURE:
<221> NAME/KEY: misc_feature
<222> LOCATION: (1)..(91)

<400> SEQUENCE: 3
cggcagcuug uugaguagag ugugagcucc guaacuaguc gcgucuucgg acgcgacuga        60
augaaauggu gaaggacggg uccagcugcu u                                      91

<210> SEQ ID NO 4
<211> LENGTH: 95
<212> TYPE: RNA
<213> ORGANISM: Artificial Sequence
<220> FEATURE:
<223> OTHER INFORMATION: synthetic nucleotide aSp9
<220> FEATURE:
<221> NAME/KEY: misc_feature
<222> LOCATION: (1)..(95)

<400> SEQUENCE: 4
ggcaggcacu uguugaguag agugugagcu ccguaacuag ucgcgucuuc ggacgcgacu        60
gaaugaaaug gugaaggacg gguccagugu cugcu                                  95

<210> SEQ ID NO 5
<211> LENGTH: 85
<212> TYPE: RNA
<213> ORGANISM: Artificial Sequence
<220> FEATURE:
<223> OTHER INFORMATION: synthetic nucleotide aSp4
<220> FEATURE:
<221> NAME/KEY: misc_feature
<222> LOCATION: (1)..(85)

<400> SEQUENCE: 5
cagcuuguug aguagagugu gagcuccgua acuagucgcg ucuucggacg cgacugaaug        60
aaauggugaa ggacgggucc agcug                                             85

<210> SEQ ID NO 6
<211> LENGTH: 91
<212> TYPE: RNA
<213> ORGANISM: Artificial Sequence
<220> FEATURE:
<223> OTHER INFORMATION: synthetic nucleotide aSp7m
<220> FEATURE:
```

```
<221> NAME/KEY: misc_feature
<222> LOCATION: (1)..(91)

<400> SEQUENCE: 6
caggcacuug uugaguagag ugugagcucc guaacuaguc gcgucuucgg acgcgacuga    60
augaaauggu gaaggacggg uccagugacu g                                  91

<210> SEQ ID NO 7
<211> LENGTH: 87
<212> TYPE: RNA
<213> ORGANISM: Artificial Sequence
<220> FEATURE:
<223> OTHER INFORMATION: synthetic nucleotide aSp5b
<220> FEATURE:
<221> NAME/KEY: misc_feature
<222> LOCATION: (1)..(87)

<400> SEQUENCE: 7
cagcuuuguu gaguagagug ugagcuccgu aacuagucgc gucuucggac gcgacugaau    60
gaaaugguga aggacggguc caagcug                                       87

<210> SEQ ID NO 8
<211> LENGTH: 89
<212> TYPE: RNA
<213> ORGANISM: Artificial Sequence
<220> FEATURE:
<223> OTHER INFORMATION: synthetic nucleotide aSp6b
<220> FEATURE:
<221> NAME/KEY: misc_feature
<222> LOCATION: (1)..(89)

<400> SEQUENCE: 8
cagcucuugu ugaguagagu gugagcuccg uaacuagucg cgucuucgga cgcgacugaa    60
ugaaauggug aaggacgggu ccagagcug                                     89

<210> SEQ ID NO 9
<211> LENGTH: 116
<212> TYPE: RNA
<213> ORGANISM: Artificial Sequence
<220> FEATURE:
<223> OTHER INFORMATION: synthetic nucleic acid sensor caSp4
<220> FEATURE:
<221> NAME/KEY: misc_feature
<222> LOCATION: (1)..(116)

<400> SEQUENCE: 9
ggaagagaug gcgacuaaaa cgacuugucg ccagcuuguu gaguagagug ugagcuccgu    60
aacuagucgc gucuucggac gcgacugaau gaaaugguga aggacggguc cagcug       116

<210> SEQ ID NO 10
<211> LENGTH: 118
<212> TYPE: RNA
<213> ORGANISM: Artificial Sequence
<220> FEATURE:
<223> OTHER INFORMATION: synthetic nucleic acid sensor caSp5a
<220> FEATURE:
<221> NAME/KEY: misc_feature
<222> LOCATION: (1)..(118)

<400> SEQUENCE: 10
ggaagagaug gcgacuaaaa cgacuugucg cgcagcuugu ugaguagagu gugagcuccg    60
uaacuagucg cgucuucgga cgcgacugaa ugaaauggug aaggacgggu ccagcugc     118

<210> SEQ ID NO 11
```

-continued

```
<211> LENGTH: 122
<212> TYPE: RNA
<213> ORGANISM: Artificial Sequence
<220> FEATURE:
<223> OTHER INFORMATION: synthetic nucleic acid sensor caSp6a
<220> FEATURE:
<221> NAME/KEY: misc_feature
<222> LOCATION: (1)..(122)

<400> SEQUENCE: 11
ggaagagaug gcgacuaaaa cgacuugucg ccggcagcuu guugaguaga gugugagcuc    60
cguaacuagu cgcgucuucg gacgcgacug aaugaaaugg ugaaggacgg guccagcugc   120
uu                                                                 122

<210> SEQ ID NO 12
<211> LENGTH: 122
<212> TYPE: RNA
<213> ORGANISM: Artificial Sequence
<220> FEATURE:
<223> OTHER INFORMATION: synthetic nucleic acid sensor caSp7
<220> FEATURE:
<221> NAME/KEY: misc_feature
<222> LOCATION: (1)..(122)

<400> SEQUENCE: 12
ggaagagaug gcgacuaaaa cgacuugucg ccaggcacuu guugaguaga gugugagcuc    60
cguaacuagu cgcgucuucg gacgcgacug aaugaaaugg ugaaggacgg guccagguc    120 ug                                                                 122

<210> SEQ ID NO 13
<211> LENGTH: 126
<212> TYPE: RNA
<213> ORGANISM: Artificial Sequence
<220> FEATURE:
<223> OTHER INFORMATION: synthetic nucleic acid sensor caSp9m'
<220> FEATURE:
<221> NAME/KEY: misc_feature
<222> LOCATION: (1)..(126)

<400> SEQUENCE: 13
ggaagagaug gcgacuaaaa cgacuugucg cggcaggcac uuguugagua gagugugagc    60
uccguaacua gucgcgucuu cggacgcgac ugaaugaaau ggugaaggac ggguccagug   120
ugugcu                                                             126

<210> SEQ ID NO 14
<211> LENGTH: 126
<212> TYPE: RNA
<213> ORGANISM: Artificial Sequence
<220> FEATURE:
<223> OTHER INFORMATION: synthetic nucleic acid sensor caSp9m''
<220> FEATURE:
<221> NAME/KEY: misc_feature
<222> LOCATION: (1)..(126)

<400> SEQUENCE: 14
ggaagagaug gcgacuaaaa cgacuugucg cggcaggcac uuguugagua gagugugagc    60
uccguaacua gucgcgucuu cggacgcgac ugaaugaaau ggugaaggac ggguccagug   120
ucggcu                                                             126

<210> SEQ ID NO 15
<211> LENGTH: 122
<212> TYPE: RNA
<213> ORGANISM: Artificial Sequence
```

<220> FEATURE:
<223> OTHER INFORMATION: synthetic nucleic acid sensor caSp7m
<220> FEATURE:
<221> NAME/KEY: misc_feature
<222> LOCATION: (1)..(122)

<400> SEQUENCE: 15
ggaagagaug gcgacuaaaa cgacuugucg ccaggcacuu guugaguaga gugugagcuc    60
cguaacuagu cgcgucuucg gacgcgacug aaugaaaugg ugaaggacgg guccagugac   120
ug                                                                 122

<210> SEQ ID NO 16
<211> LENGTH: 118
<212> TYPE: RNA
<213> ORGANISM: Artificial Sequence
<220> FEATURE:
<223> OTHER INFORMATION: synthetic nucleic acid sensor caSp5b
<220> FEATURE:
<221> NAME/KEY: misc_feature
<222> LOCATION: (1)..(118)

<400> SEQUENCE: 16
ggaagagaug gcgacuaaaa cgacuugucg ccagcuuugu ugaguagagu gugagcuccg    60
uaacuagucg cgucuucgga cgcgacugaa ugaaauggug aaggacgggu ccaagcug    118

<210> SEQ ID NO 17
<211> LENGTH: 154
<212> TYPE: RNA
<213> ORGANISM: Artificial Sequence
<220> FEATURE:
<223> OTHER INFORMATION: synthetic nucleic acid sensor caSp4A
<220> FEATURE:
<221> NAME/KEY: misc_feature
<222> LOCATION: (1)..(154)

<400> SEQUENCE: 17
ggaagagaug gcgacuaaaa cgacuugucg ccagcuuguu gaguagagug ugagcuccgu    60
aacuagucgc gucuucggac gcgacugaau gaaaugguga aggacggguc cagcugauca   120
acacugcaca ccagacagca agauccuaua uaua                              154

<210> SEQ ID NO 18
<211> LENGTH: 160
<212> TYPE: RNA
<213> ORGANISM: Artificial Sequence
<220> FEATURE:
<223> OTHER INFORMATION: synthetic nucleic acid sensor caSp7mA
<220> FEATURE:
<221> NAME/KEY: misc_feature
<222> LOCATION: (1)..(160)

<400> SEQUENCE: 18
ggaagagaug gcgacuaaaa cgacuugucg ccaggcacuu guugaguaga gugugagcuc    60
cguaacuagu cgcgucuucg gacgcgacug aaugaaaugg ugaaggacgg guccagugac   120
ugaucaacac ugcacaccag acagcaagau ccuauauaua                        160

<210> SEQ ID NO 19
<211> LENGTH: 38
<212> TYPE: DNA
<213> ORGANISM: Artificial Sequence
<220> FEATURE:
<223> OTHER INFORMATION: synthetic nucleotide D2 Alexa 647
<220> FEATURE:
<221> NAME/KEY: misc_feature
<222> LOCATION: (1)..(38)

```
<400> SEQUENCE: 19
tatatatagg atcttgctgt ctggtgtgca gtgttgat                              38

<210> SEQ ID NO 20
<211> LENGTH: 95
<212> TYPE: RNA
<213> ORGANISM: Artificial Sequence
<220> FEATURE:
<223> OTHER INFORMATION: synthetic nucleotide caSp4SplitA
<220> FEATURE:
<221> NAME/KEY: misc_feature
<222> LOCATION: (1)..(95)

<400> SEQUENCE: 20
ggaagagaug gcgacuaaaa cgacuugucg ccagcuuguu gaguagagug ugagcuccgu     60
aacuagucgc guccggcgua ccguaccgua cccug                               95

<210> SEQ ID NO 21
<211> LENGTH: 99
<212> TYPE: RNA
<213> ORGANISM: Artificial Sequence
<220> FEATURE:
<223> OTHER INFORMATION: synthetic nucleotide caSp4SplitB
<220> FEATURE:
<221> NAME/KEY: misc_feature
<222> LOCATION: (1)..(99)

<400> SEQUENCE: 21
aucaacacug cacaccagac agcaagaucc uauauauaca ggguacggua cgguacgccg     60
gacgcgacug aaugaaaugg ugaaggacgg guccagcug                           99

<210> SEQ ID NO 22
<211> LENGTH: 120
<212> TYPE: RNA
<213> ORGANISM: Artificial Sequence
<220> FEATURE:
<223> OTHER INFORMATION: synthetic nucleic acid sensor caSp6b
<220> FEATURE:
<221> NAME/KEY: misc_feature
<222> LOCATION: (1)..(120)

<400> SEQUENCE: 22
ggaagagaug gcgacuaaaa cgacuugucg ccagcucuug uugaguagag ugugagcucc     60
guaacuaguc gcgucuucgg acgcgacuga augaaauggu gaaggacggg uccagagcug    120

<210> SEQ ID NO 23
<211> LENGTH: 31
<212> TYPE: RNA
<213> ORGANISM: Artificial Sequence
<220> FEATURE:
<223> OTHER INFORMATION: synthetic nucleotide cAMP aptamer
<220> FEATURE:
<221> NAME/KEY: misc_feature
<222> LOCATION: (1)..(31)

<400> SEQUENCE: 23
ggaagagaug gcgacuaaaa cgacuugucg c                                   31

<210> SEQ ID NO 24
<211> LENGTH: 87
<212> TYPE: RNA
<213> ORGANISM: Artificial Sequence
<220> FEATURE:
<223> OTHER INFORMATION: synthetic nucleotide Spinach
<220> FEATURE:
```

```
<221> NAME/KEY: misc_feature
<222> LOCATION: (1)..(87)

<400> SEQUENCE: 24
gacgcgacug aaugaaaugg ugaaggacgg guccagcugc uucggcagcu uguugaguag    60
agugugagcu ccguaacuag ucgcguc                                       87

<210> SEQ ID NO 25
<211> LENGTH: 76
<212> TYPE: DNA
<213> ORGANISM: Artificial Sequence
<220> FEATURE:
<223> OTHER INFORMATION: synthetic nucleotide caSp4DNA-1
<220> FEATURE:
<221> NAME/KEY: misc_feature
<222> LOCATION: (1)..(76)

<400> SEQUENCE: 25
taatacgact cactatagga agagatggcg actaaaacga cttgtcgcca gcttgttgag    60
tagagtgtga gctccg                                                   76

<210> SEQ ID NO 26
<211> LENGTH: 76
<212> TYPE: DNA
<213> ORGANISM: Artificial Sequence
<220> FEATURE:
<223> OTHER INFORMATION: synthetic nucleotide caSp4DNA-2
<220> FEATURE:
<221> NAME/KEY: misc_feature
<222> LOCATION: (1)..(76)

<400> SEQUENCE: 26
cagctggacc cgtccttcac catttcattc agtcgcgtcc gaagacgcga ctagttacgg    60
agctcacact ctactc                                                   76

<210> SEQ ID NO 27
<211> LENGTH: 73
<212> TYPE: DNA
<213> ORGANISM: Artificial Sequence
<220> FEATURE:
<223> OTHER INFORMATION: synthetic nucleotide caSp4SplitBDNA1
<220> FEATURE:
<221> NAME/KEY: misc_feature
<222> LOCATION: (1)..(73)

<400> SEQUENCE: 27
taatacgact cactataggg atcaacactg cacaccagac agcaagatcc tatatataca    60
gggtacggta cgg                                                      73

<210> SEQ ID NO 28
<211> LENGTH: 74
<212> TYPE: DNA
<213> ORGANISM: Artificial Sequence
<220> FEATURE:
<223> OTHER INFORMATION: synthetic nucleotide caSp4SplitBDNA2
<220> FEATURE:
<221> NAME/KEY: misc_feature
<222> LOCATION: (1)..(74)

<400> SEQUENCE: 28
cagctggacc cgtccttcac catttcattc agtcgcgtcc ggcgtaccgt accgtaccct    60
gtatatatag gatc                                                     74

<210> SEQ ID NO 29
```

```
<210> SEQ ID NO 29
<211> LENGTH: 25
<212> TYPE: DNA
<213> ORGANISM: Artificial Sequence
<220> FEATURE:
<223> OTHER INFORMATION: synthetic primer FPcaSp4
<220> FEATURE:
<221> NAME/KEY: misc_feature
<222> LOCATION: (1)..(25)

<400> SEQUENCE: 29
taatacgact cactataggc agaga                                    25

<210> SEQ ID NO 30
<211> LENGTH: 30
<212> TYPE: DNA
<213> ORGANISM: Artificial Sequence
<220> FEATURE:
<223> OTHER INFORMATION: synthetic primer RPcaSp4
<220> FEATURE:
<221> NAME/KEY: misc_feature
<222> LOCATION: (1)..(30)

<400> SEQUENCE: 30
cagctggacc cgtccttcac catttcattc                               30

<210> SEQ ID NO 31
<211> LENGTH: 35
<212> TYPE: DNA
<213> ORGANISM: Artificial Sequence
<220> FEATURE:
<223> OTHER INFORMATION: synthetic primer FPIVTcaSpn
<220> FEATURE:
<221> NAME/KEY: misc_feature
<222> LOCATION: (1)..(35)

<400> SEQUENCE: 31
attcgccctt taatacgact cactataggc agaga                         35

<210> SEQ ID NO 32
<211> LENGTH: 28
<212> TYPE: DNA
<213> ORGANISM: Artificial Sequence
<220> FEATURE:
<223> OTHER INFORMATION: synthetic primer RPcaSp5aPartA
<220> FEATURE:
<221> NAME/KEY: misc_feature
<222> LOCATION: (1)..(28)

<400> SEQUENCE: 32
tctactcaac aagctgcgcg acaagtcg                                 28

<210> SEQ ID NO 33
<211> LENGTH: 27
<212> TYPE: DNA
<213> ORGANISM: Artificial Sequence
<220> FEATURE:
<223> OTHER INFORMATION: synthetic primer FPcaSp5aPartB
<220> FEATURE:
<221> NAME/KEY: misc_feature
<222> LOCATION: (1)..(27)

<400> SEQUENCE: 33
cgacttgtcg cgcagcttgt tgagtag                                  27

<210> SEQ ID NO 34
<211> LENGTH: 27
<212> TYPE: DNA
<213> ORGANISM: Artificial Sequence
<220> FEATURE:
```

```
<223> OTHER INFORMATION: synthetic primer RPcaSp5a
<220> FEATURE:
<221> NAME/KEY: misc_feature
<222> LOCATION: (1)..(27)

<400> SEQUENCE: 34
gcagctggac ccgtccttca ccatttc                                              27

<210> SEQ ID NO 35
<211> LENGTH: 27
<212> TYPE: DNA
<213> ORGANISM: Artificial Sequence
<220> FEATURE:
<223> OTHER INFORMATION: synthetic primer RPcaSp5bPartA
<220> FEATURE:
<221> NAME/KEY: misc_feature
<222> LOCATION: (1)..(27)

<400> SEQUENCE: 35
ctactcaaca aagctggcga caagtcg                                              27

<210> SEQ ID NO 36
<211> LENGTH: 27
<212> TYPE: DNA
<213> ORGANISM: Artificial Sequence
<220> FEATURE:
<223> OTHER INFORMATION: synthetic primer FPcaSp5bPartB
<220> FEATURE:
<221> NAME/KEY: misc_feature
<222> LOCATION: (1)..(27)

<400> SEQUENCE: 36
cgacttgtcg ccagctttgt tgagtag                                              27

<210> SEQ ID NO 37
<211> LENGTH: 27
<212> TYPE: DNA
<213> ORGANISM: Artificial Sequence
<220> FEATURE:
<223> OTHER INFORMATION: synthetic primer RPcaSp5b
<220> FEATURE:
<221> NAME/KEY: misc_feature
<222> LOCATION: (1)..(27)

<400> SEQUENCE: 37
cagcttggac ccgtccttca ccatttc                                              27

<210> SEQ ID NO 38
<211> LENGTH: 30
<212> TYPE: DNA
<213> ORGANISM: Artificial Sequence
<220> FEATURE:
<223> OTHER INFORMATION: synthetic primer RPcaSp6aPartA
<220> FEATURE:
<221> NAME/KEY: misc_feature
<222> LOCATION: (1)..(30)

<400> SEQUENCE: 38
tctactcaac aagctgccgg cgacaagtcg                                           30

<210> SEQ ID NO 39
<211> LENGTH: 29
<212> TYPE: DNA
<213> ORGANISM: Artificial Sequence
<220> FEATURE:
<223> OTHER INFORMATION: synthetic primer FPcaSp6aPartB
<220> FEATURE:
<221> NAME/KEY: misc_feature
<222> LOCATION: (1)..(29)
```

<400> SEQUENCE: 39
cgacttgtcg ccggcagctt gttgagtag                                29

<210> SEQ ID NO 40
<211> LENGTH: 29
<212> TYPE: DNA
<213> ORGANISM: Artificial Sequence
<220> FEATURE:
<223> OTHER INFORMATION: synthetic primer RPcaSp6a
<220> FEATURE:
<221> NAME/KEY: misc_feature
<222> LOCATION: (1)..(29)

<400> SEQUENCE: 40
aagcagctgg acccgtcctt caccatttc                                29

<210> SEQ ID NO 41
<211> LENGTH: 28
<212> TYPE: DNA
<213> ORGANISM: Artificial Sequence
<220> FEATURE:
<223> OTHER INFORMATION: synthetic primer RPcaSp6bPart A
<220> FEATURE:
<221> NAME/KEY: misc_feature
<222> LOCATION: (1)..(28)

<400> SEQUENCE: 41
ctactcaaca agagctggcg acaagtcg                                 28

<210> SEQ ID NO 42
<211> LENGTH: 28
<212> TYPE: DNA
<213> ORGANISM: Artificial Sequence
<220> FEATURE:
<223> OTHER INFORMATION: synthetic primer FPcaSp6bPartB
<220> FEATURE:
<221> NAME/KEY: misc_feature
<222> LOCATION: (1)..(28)

<400> SEQUENCE: 42
cgacttgtcg ccagctcttg ttgagtag                                 28

<210> SEQ ID NO 43
<211> LENGTH: 28
<212> TYPE: DNA
<213> ORGANISM: Artificial Sequence
<220> FEATURE:
<223> OTHER INFORMATION: synthetic primer RPcaSp6b
<220> FEATURE:
<221> NAME/KEY: misc_feature
<222> LOCATION: (1)..(28)

<400> SEQUENCE: 43
cagctctgga cccgtccttc accatttc                                 28

<210> SEQ ID NO 44
<211> LENGTH: 30
<212> TYPE: DNA
<213> ORGANISM: Artificial Sequence
<220> FEATURE:
<223> OTHER INFORMATION: synthetic primer RPcaSp7PartA
<220> FEATURE:
<221> NAME/KEY: misc_feature
<222> LOCATION: (1)..(30)

<400> SEQUENCE: 44
tctactcaac aagtgcctgg cgacaagtcg                               30

<210> SEQ ID NO 45
<211> LENGTH: 30
<212> TYPE: DNA
<213> ORGANISM: Artificial Sequence
<220> FEATURE:
<223> OTHER INFORMATION: synthetic primer FPcaSp7PartB
<220> FEATURE:
<221> NAME/KEY: misc_feature
<222> LOCATION: (1)..(30)

<400> SEQUENCE: 45
acgacttgtc gccaggcact tgttgagtag                                 30

<210> SEQ ID NO 46
<211> LENGTH: 29
<212> TYPE: DNA
<213> ORGANISM: Artificial Sequence
<220> FEATURE:
<223> OTHER INFORMATION: synthetic primer RPcaSp7
<220> FEATURE:
<221> NAME/KEY: misc_feature
<222> LOCATION: (1)..(29)

<400> SEQUENCE: 46
cagacactgg acccgtcctt caccatttc                                  29

<210> SEQ ID NO 47
<211> LENGTH: 28
<212> TYPE: DNA
<213> ORGANISM: Artificial Sequence
<220> FEATURE:
<223> OTHER INFORMATION: synthetic primer RPcaSp7m
<220> FEATURE:
<221> NAME/KEY: misc_feature
<222> LOCATION: (1)..(28)

<400> SEQUENCE: 47
cagtcactgg acccgtcctt caccttc                                    28

<210> SEQ ID NO 48
<211> LENGTH: 33
<212> TYPE: DNA
<213> ORGANISM: Artificial Sequence
<220> FEATURE:
<223> OTHER INFORMATION: synthetic primer RPcaSp9PartA
<220> FEATURE:
<221> NAME/KEY: misc_feature
<222> LOCATION: (1)..(33)

<400> SEQUENCE: 48
ctctactcaa caagtgcctg ccgcgacaag tcg                             33

<210> SEQ ID NO 49
<211> LENGTH: 35
<212> TYPE: DNA
<213> ORGANISM: Artificial Sequence
<220> FEATURE:
<223> OTHER INFORMATION: synthetic primer FPcaSp9PartB
<220> FEATURE:
<221> NAME/KEY: misc_feature
<222> LOCATION: (1)..(35)

<400> SEQUENCE: 49
aacgacttgt cgcggcaggc acttgttgag tagag                           35

<210> SEQ ID NO 50
<211> LENGTH: 26

<212> TYPE: DNA
<213> ORGANISM: Artificial Sequence
<220> FEATURE:
<223> OTHER INFORMATION: synthetic primer RPcaSp9
<220> FEATURE:
<221> NAME/KEY: misc_feature
<222> LOCATION: (1)..(26)

<400> SEQUENCE: 50
agcagacact ggacccgtcc ttcacc                                   26

<210> SEQ ID NO 51
<211> LENGTH: 30
<212> TYPE: DNA
<213> ORGANISM: Artificial Sequence
<220> FEATURE:
<223> OTHER INFORMATION: synthetic primer RPcaSp9m
<220> FEATURE:
<221> NAME/KEY: misc_feature
<222> LOCATION: (1)..(30)

<400> SEQUENCE: 51
agcacacact ggacccgtcc ttcacctttc                               30

<210> SEQ ID NO 52
<211> LENGTH: 30
<212> TYPE: DNA
<213> ORGANISM: Artificial Sequence
<220> FEATURE:
<223> OTHER INFORMATION: synthetic primer RPcaSp9m'
<220> FEATURE:
<221> NAME/KEY: misc_feature
<222> LOCATION: (1)..(30)

<400> SEQUENCE: 52
agcacacact ggacccgtcc ttcacctttc                               30

<210> SEQ ID NO 53
<211> LENGTH: 30
<212> TYPE: DNA
<213> ORGANISM: Artificial Sequence
<220> FEATURE:
<223> OTHER INFORMATION: synthetic primer RPcaSp9m''
<220> FEATURE:
<221> NAME/KEY: misc_feature
<222> LOCATION: (1)..(30)

<400> SEQUENCE: 53
agccgacact ggacccgtcc ttcacctttc                               30

<210> SEQ ID NO 54
<211> LENGTH: 30
<212> TYPE: DNA
<213> ORGANISM: Artificial Sequence
<220> FEATURE:
<223> OTHER INFORMATION: synthetic primer FPcaSp4SplitB
<220> FEATURE:
<221> NAME/KEY: misc_feature
<222> LOCATION: (1)..(30)

<400> SEQUENCE: 54
taatacgact cactataggg atcaacactg                               30

<210> SEQ ID NO 55
<211> LENGTH: 30
<212> TYPE: DNA
<213> ORGANISM: Artificial Sequence
<220> FEATURE:
<223> OTHER INFORMATION: synthetic primer RPcaSp4SplitB
<220> FEATURE:
<221> NAME/KEY: misc_feature
<222> LOCATION: (1)..(30)

<400> SEQUENCE: 55
attcgccctt taatacgact cactataggg                                    30

<210> SEQ ID NO 56
<211> LENGTH: 39
<212> TYPE: DNA
<213> ORGANISM: Artificial Sequence
<220> FEATURE:
<223> OTHER INFORMATION: synthetic primer RPcaSp4SplitA
<220> FEATURE:
<221> NAME/KEY: misc_feature
<222> LOCATION: (1)..(39)

<400> SEQUENCE: 56
cagggtacgg tacggtacgc cggacgcgac tagttacgg                          39

<210> SEQ ID NO 57
<211> LENGTH: 59
<212> TYPE: DNA
<213> ORGANISM: Artificial Sequence
<220> FEATURE:
<223> OTHER INFORMATION: synthetic primer RPcaSp4A
<220> FEATURE:
<221> NAME/KEY: misc_feature
<222> LOCATION: (1)..(59)

<400> SEQUENCE: 57
tatatatagg atcttgctgt ctggtgtgca gtgttgatca gctggacccg tccttcacc    59

<210> SEQ ID NO 58
<211> LENGTH: 61
<212> TYPE: DNA
<213> ORGANISM: Artificial Sequence
<220> FEATURE:
<223> OTHER INFORMATION: synthetic primer RPcaSp7mA
<220> FEATURE:
<221> NAME/KEY: misc_feature
<222> LOCATION: (1)..(61)

<400> SEQUENCE: 58
tatatatagg atcttgctgt ctggtgtgca gtgttgatag tcactggacc cgtccttcac   60
c                                                                   61

<210> SEQ ID NO 59
<211> LENGTH: 30
<212> TYPE: DNA
<213> ORGANISM: Artificial Sequence
<220> FEATURE:
<223> OTHER INFORMATION: synthetic primer RPcaSp7nePartA
<220> FEATURE:
<221> NAME/KEY: misc_feature
<222> LOCATION: (1)..(30)

<400> SEQUENCE: 59
tctactcaac aagtccctgg cgacaagtcg                                    30

<210> SEQ ID NO 60
<211> LENGTH: 30
<212> TYPE: DNA
<213> ORGANISM: Artificial Sequence
<220> FEATURE:
<223> OTHER INFORMATION: synthetic primer FPcaSp7nePartB
<220> FEATURE:
<221> NAME/KEY: misc_feature

```
<222> LOCATION: (1)..(30)

<400> SEQUENCE: 60
acgacttgtc gccagggact tgttgagtag                                        30

<210> SEQ ID NO 61
<211> LENGTH: 29
<212> TYPE: DNA
<213> ORGANISM: Artificial Sequence
<220> FEATURE:
<223> OTHER INFORMATION: synthetic primer RPcaSp7ne
<220> FEATURE:
<221> NAME/KEY: misc_feature
<222> LOCATION: (1)..(29)

<400> SEQUENCE: 61
aagagactgg acccgtcctt caccatttc                                         29

<210> SEQ ID NO 62
<211> LENGTH: 122
<212> TYPE: RNA
<213> ORGANISM: Artificial Sequence
<220> FEATURE:
<223> OTHER INFORMATION: synthetic nucleic acid sensor caSp7NE
<220> FEATURE:
<221> NAME/KEY: misc_feature
<222> LOCATION: (1)..(122)

<400> SEQUENCE: 62
ggaagagaug gcgacuaaaa cgacuugucg ccagggacuu guugaguaga gugugagcuc       60
cguaacuagu cgcgucuucg gacgcgacug aaugaaaugg ugaaggacgg guccagucuc      120
uu                                                                     122

<210> SEQ ID NO 63
<211> LENGTH: 143
<212> TYPE: DNA
<213> ORGANISM: Artificial Sequence
<220> FEATURE:
<223> OTHER INFORMATION: Synthetic Duplex IVT DNA positive strand
<220> FEATURE:
<221> NAME/KEY: misc_feature
<222> LOCATION: (1)..(143)

<400> SEQUENCE: 63
attcgccctt taatacgact cactatagga agagatggcg actaaaacga cttgtcgcca       60
gcttgttgag tagagtgtga gctccgtaac tagtcgcgtc ttcggacgcg actgaatgaa      120
atggtgaagg acgggtccag ctg                                              143

<210> SEQ ID NO 64
<211> LENGTH: 143
<212> TYPE: DNA
<213> ORGANISM: Artificial Sequence
<220> FEATURE:
<223> OTHER INFORMATION: Synthetic Duplex IVT DNA negative strand
<220> FEATURE:
<221> NAME/KEY: misc_feature
<222> LOCATION: (1)..(143)

<400> SEQUENCE: 64
taagcgggaa attatgctga gtgatatcct tctctaccgc tgattttgct gaacagcggt       60
cgaacaactc atctcacact cgaggcattg atcagcgcag aagcctgcgc tgacttactt      120
taccacttcc tgcccaggtc gac                                              143
```